United States Patent
Toupin et al.

(10) Patent No.: US 10,417,387 B2
(45) Date of Patent: Sep. 17, 2019

(54) SYSTEM, METHOD, AND NON-TRANSITORY COMPUTER-READABLE STORAGE MEDIA FOR MOBILE CHECK-IN IN RETAIL STORE

(71) Applicant: Wal-Mart Stores, Inc., Bentonville, AR (US)

(72) Inventors: Justin Toupin, San Francisco, CA (US); Nathan Thomas Diepenbrock, Highlands Ranch, CO (US)

(73) Assignee: WALMART APOLLO, LLC, Bentonville, AR (US)

( * ) Notice: Subject to any disclaimer, the term of this patent is extended or adjusted under 35 U.S.C. 154(b) by 628 days.

(21) Appl. No.: 15/009,611

(22) Filed: Jan. 28, 2016

(65) Prior Publication Data

US 2017/0220764 A1   Aug. 3, 2017

(51) Int. Cl.
*G06F 19/00* (2018.01)

(52) U.S. Cl.
CPC .................. *G06F 19/3456* (2013.01)

(58) Field of Classification Search
None
See application file for complete search history.

(56) References Cited

U.S. PATENT DOCUMENTS

| | | |
|---|---|---|
| 6,543,683 B2 | 4/2003 | Hoffman |
| 6,711,460 B1 | 3/2004 | Reese |
| 6,898,598 B2 | 5/2005 | Himmel et al. |
| 7,487,912 B2 | 2/2009 | Seifert et al. |
| 7,747,695 B1 | 6/2010 | Morris et al. |
| 8,606,698 B2 | 12/2013 | Schultz et al. |
| 8,612,245 B2 * | 12/2013 | Marshall ............ G06F 19/324 705/2 |
| 9,043,217 B2 | 5/2015 | Cashman et al. |

(Continued)

FOREIGN PATENT DOCUMENTS

| | | |
|---|---|---|
| WO | 2000075834 A2 | 12/2000 |
| WO | 2007134378 A1 | 11/2007 |
| WO | 2012064026 A2 | 5/2012 |

OTHER PUBLICATIONS

Website: www.blueapron.com—Blue Apron: Fresh Ingredients, Original Recipes, Delivered to You; downloaded Feb. 3, 2016; 29 pages total. Feb. 3, 2016.

*Primary Examiner* — Michael Tomaszewski
*Assistant Examiner* — Jay M. Patel
(74) *Attorney, Agent, or Firm* — Bryan Cave Leighton Paisner LLP

(57) ABSTRACT

A system, method, and non-transitory computer-readable storage media for mobile check-in in a retail store includes a computer system configured to receive input from and provide output to a mobile computing application for a retail store running on a mobile computing device of a customer. The computer system is configured to determine a location of the customer entering or in the retail store, to confirm that the customer has at least one prescription fill order pending with a pharmacy of the retail store, to prioritize the at least one prescription fill order to a top of a workflow of a pharmacist in the pharmacy of the retail store, and transmitting a communication to the mobile computing device of the customer that the customer will be notified when the at least one prescription fill order is ready to be picked up at the pharmacy of the retail store.

21 Claims, 14 Drawing Sheets

(56) References Cited

U.S. PATENT DOCUMENTS

| | | |
|---|---|---|
| 9,195,959 B1 | 11/2015 | Lopez et al. |
| 9,607,345 B1 | 3/2017 | Hendren et al. |
| 2002/0073043 A1 | 6/2002 | Herman et al. |
| 2003/0096616 A1 | 5/2003 | Speight et al. |
| 2003/0120607 A1 | 6/2003 | Piotrowski |
| 2003/0187672 A1 | 10/2003 | Gibson |
| 2003/0216950 A1* | 11/2003 | Chen ............... G06Q 10/087 705/26.81 |
| 2004/0204954 A1 | 10/2004 | Lacko |
| 2004/0236635 A1* | 11/2004 | Publicover ........ G06Q 10/08 705/26.81 |
| 2005/0165651 A1 | 7/2005 | Mohan |
| 2006/0004607 A1* | 1/2006 | Marshall ............. G06Q 30/02 705/2 |
| 2007/0088624 A1* | 4/2007 | Vaughn ............... G06Q 30/02 705/15 |
| 2007/0124170 A1 | 5/2007 | Cabell et al. |
| 2007/0150375 A1* | 6/2007 | Yang ................. G06Q 10/08 705/339 |
| 2007/0204169 A1 | 8/2007 | Bahl et al. |
| 2007/0226071 A1* | 9/2007 | Kern ................. G06Q 10/087 705/26.5 |
| 2008/0133283 A1 | 6/2008 | Backer et al. |
| 2009/0076875 A1 | 3/2009 | Lert, Jr. et al. |
| 2009/0125331 A1* | 5/2009 | Pamsgaard ......... A61K 31/343 705/3 |
| 2009/0181131 A1 | 7/2009 | Forbes-Roberts |
| 2009/0271265 A1 | 10/2009 | Lay et al. |
| 2010/0121807 A1* | 5/2010 | Perrier ................. G06Q 30/02 706/47 |
| 2011/0016007 A1 | 1/2011 | Shiftan et al. |
| 2011/0125519 A1 | 5/2011 | Dhoble |
| 2011/0231272 A1 | 9/2011 | Englund et al. |
| 2011/0307265 A1* | 12/2011 | Bannis ............... G06Q 50/22 705/2 |
| 2011/0307547 A1 | 12/2011 | Backer et al. |
| 2011/0313790 A1 | 12/2011 | Yao |
| 2011/0321127 A1* | 12/2011 | Pitroda ............... G06Q 20/02 726/3 |
| 2012/0072311 A1* | 3/2012 | Khan .................. G06Q 30/06 705/26.81 |
| 2012/0078673 A1* | 3/2012 | Koke ................. G06Q 10/06 705/7.13 |
| 2012/0084391 A1 | 4/2012 | Patel et al. |
| 2012/0114116 A1 | 5/2012 | Sulaiman et al. |
| 2012/0123674 A1 | 5/2012 | Perks et al. |
| 2012/0166298 A1 | 6/2012 | Smith et al. |
| 2012/0191573 A1* | 7/2012 | Miller ................ G06Q 20/204 705/26.81 |
| 2012/0221446 A1 | 8/2012 | Grigg et al. |
| 2012/0290609 A1 | 11/2012 | Britt |
| 2013/0159858 A1 | 6/2013 | Joffray et al. |
| 2013/0173287 A1* | 7/2013 | Cashman ............ E04H 3/08 705/2 |
| 2013/0173403 A1 | 7/2013 | Grigg et al. |
| 2013/0179180 A1 | 7/2013 | Patra |
| 2013/0196297 A1 | 8/2013 | Anwar |
| 2013/0224694 A1 | 8/2013 | Moore et al. |
| 2013/0290145 A1 | 10/2013 | Durst, Jr. |
| 2014/0080102 A1 | 3/2014 | Krishna |
| 2014/0156297 A1 | 6/2014 | Schaefer et al. |
| 2014/0188648 A1 | 7/2014 | Argue et al. |
| 2014/0222482 A1 | 8/2014 | Gautam et al. |
| 2014/0244296 A1 | 8/2014 | Linn et al. |
| 2014/0258022 A1 | 9/2014 | Zamer et al. |
| 2014/0279269 A1* | 9/2014 | Brantley ............ G06Q 30/0635 705/26.81 |
| 2014/0359422 A1* | 12/2014 | Bassett, Jr. ......... G16B 20/00 715/230 |
| 2015/0161353 A1* | 6/2015 | Emerson ............ G06F 19/3456 705/2 |
| 2015/0242592 A1* | 8/2015 | Weiss ................ G06F 19/3456 705/2 |
| 2015/0261934 A1* | 9/2015 | Miller ................ G06F 19/3456 705/3 |
| 2015/0285775 A1 | 10/2015 | Gurumohan et al. |
| 2015/0294084 A1* | 10/2015 | McCauley .......... G06F 19/3456 705/2 |
| 2015/0294387 A1 | 10/2015 | Karmazyn et al. |
| 2016/0205180 A1 | 7/2016 | Jan et al. |
| 2016/0364547 A1 | 12/2016 | Love et al. |
| 2017/0213271 A1 | 7/2017 | Nelms et al. |
| 2017/0220649 A1 | 8/2017 | Toupin |
| 2017/0220684 A1* | 8/2017 | Toupin ............... G06F 16/9535 |
| 2017/0220741 A1 | 8/2017 | Toupin et al. |
| 2017/0220761 A1 | 8/2017 | Toupin et al. |
| 2017/0220762 A1 | 8/2017 | Toupin et al. |
| 2017/0220763 A1 | 8/2017 | Toupin et al. |
| 2017/0220765 A1 | 8/2017 | Toupin et al. |
| 2017/0220770 A1 | 8/2017 | Toupin et al. |
| 2017/0220771 A1 | 8/2017 | Toupin et al. |
| 2017/0221123 A1 | 8/2017 | Toupin |
| 2017/0221129 A1 | 8/2017 | Toupin |
| 2017/0242976 A1 | 8/2017 | Howieson et al. |
| 2018/0130548 A1 | 5/2018 | Fisher |

* cited by examiner

SYSTEM, METHOD, AND NON-TRANSITORY COMPUTER-READABLE STORAGE MEDIA FOR MOBILE CHECK-IN IN RETAIL STORE

COPYRIGHT NOTICE

The figures included herein contain material that is subject to copyright protection. The copyright owner has no objection to the facsimile reproduction by anyone of this patent document as it appears in the U.S. Patent and Trademark Office, patent file or records, but reserves all copyrights whatsoever in the subject matter presented herein.

BACKGROUND OF THE INVENTION

1. Field of the Invention

The present invention relates generally to online transactional processing for pharmacies for retail stores and, more particularly, to a system, method, and non-transitory computer-readable storage media for mobile check-in at a pharmacy of a retail store and that that monitor activities of pharmacy customers, determine potential drug interactions, and generate and displays product information via a website in response to potential drug interactions.

2. Description of the Related Art

Many pharmacy consumers or customers desire to deliver and/or obtain their pharmaceutical medications being prescribed to them either directly or remotely, e.g., on-line, through the Internet, or using a specially designed application or app on a personal computer or mobile device, such as a tablet or cell phone. In addition, pharmacy customers may have at least one prescription fill order that needs to be filled by a pharmacist at a pharmacy of a retail store. For example, the customer may have a prescription fill order for a sexual transmitted disease that is delivered to the pharmacy of the retail store. Sometimes when the customer enters the retail store, the customer proceeds directly to the pharmacy. When the customer arrives at the pharmacy, the prescription fill order may not have been filled or is not ready for pick-up by the customer. In other situations, the customer has to tell someone in the pharmacy that they are there to pick up the prescription filled according to the prescription fill order, which is undesired.

Other known systems allow customers to search drug databases for the names of particular pharmaceutical drugs, select one or more drugs stored in the database, and display information related to the selected drugs. However, because of the increasing number of pharmaceutical drugs being made available to consumers and the amount of drug information associated with the pharmaceutical drugs, consumer may become frustrated with the lack of relevant information being provided by known systems. In addition, because of the number of records that may be included in a drug database, at least some known search engines require significant computing time and resources to generate and display the sorted drug lists to the consumer. As the amount of records being included in a database increases, the amount of computing resources that are required to perform the search functions increase, thus reducing the overall performance of known web hosting systems.

It is, therefore, desirable to provide a new system, method, and non-transitory computer-readable storage media that allows a customer to have a prescription order filled by the time they arrive at a pharmacy of a retail store. It is also desirable to provide a new system, method, and non-transitory computer-readable storage media that allows a customer to check-in ahead of time to pick-up their prescription that has been filled according to a previously delivered prescription fill order at a pharmacy of a retail store. It is further desirable to provide a new system, method, and non-transitory computer-readable storage media that provides a mobile check-in so that the customer does not have to tell someone in the pharmacy that they are there to pick up a prescription filled according to a previously delivered prescription fill order at a pharmacy of a retail store. Thus, there is a need in the art to provide a system, method, and non-transitory computer-readable storage media for mobile check-in for a pharmacy in a retail store that meets at least one of these desires.

SUMMARY OF THE INVENTION

In different embodiments of the present invention, systems, methods, and non-transitory computer-readable storage media are provided for generating, communicating, and displaying information to users via mobile computing devices.

Accordingly, the present invention provides a system including a computer system configured to receive input from and provide output to a mobile computer application for a retail store running on a mobile computing device of a customer. The computer system is configured to determine a location of the customer entering or in the retail store, to confirm that the customer has at least one prescription fill order pending with a pharmacy of the retail store, to prioritize the at least one prescription fill order to a top of a workflow of a pharmacist in the pharmacy of the retail store, and transmitting a communication to the mobile computing device of the customer that the customer will be notified when the at least one prescription fill order is ready to be picked up at the pharmacy of the retail store.

In addition, the present invention provides a method including the steps of determining, by a computer system, a location of a customer entering or in a retail store and confirming, by the computer system, that the customer has at least one prescription fill order pending with a pharmacy of the retail store. The method also includes the steps of prioritizing, by the computer system, the at least one prescription fill order to a top of a workflow of a pharmacist in the pharmacy of the retail store and transmitting, by the computer system, a communication to a mobile computing device of the customer that the customer will be notified when the at least one prescription fill order is ready to be picked up at the pharmacy of the retail store.

Further, the present invention provides one or more non-transitory computer-readable storage media, having computer-executable instructions embodied thereon, wherein when executed by at least one processor, the computer-executable instructions cause the processor to determine a location of a customer entering or in a retail store and confirm that the customer has at least one prescription fill order pending with a pharmacy of the retail store. The computer-executable instructions also cause the processor to prioritize the at least one prescription fill order to a top of a workflow of a pharmacist in the pharmacy of the retail store and transmit a communication to a mobile computing device of the customer that the customer will be notified when the at least one prescription fill order is ready to be picked up at the pharmacy of the retail store.

One advantage of the present invention is that a new system, method, and non-transitory computer-readable storage media is provided for mobile check-in with a pharmacy of a retail store. Another advantage of the present invention is that the system, method, and non-transitory computer-readable storage media allows a customer to have a prescription fill order filled and ready for pick-up by the time the customer reaches the pharmacy in the retail store. Yet another advantage of the present invention is that the system, method, and non-transitory computer-readable storage media knows when the customer is in the retail store and checks to see if the customer has at least one prescription fill order to fill or is in the process of being filled such that it tells the pharmacy to move the at least one prescription fill order to a top of the pharmacy workflow. Still another advantage of the present invention is that the system, method, and non-transitory computer-readable storage media automatically knows when the customer is at the pharmacy so that the customer does not have to tell anyone that the customer is at the pharmacy to pick-up a prescription fill according to a previously delivered prescription fill order.

Other features and advantages of the present invention will be readily appreciated, as the same becomes better understood, after reading the subsequent description taken in conjunction with the accompanying drawings.

BRIEF DESCRIPTION OF THE DRAWINGS

Non-limiting and non-exhaustive embodiments of the present invention are described with reference to the following figures, wherein like reference numerals refer to like parts throughout the various views unless otherwise specified.

Figure 1:
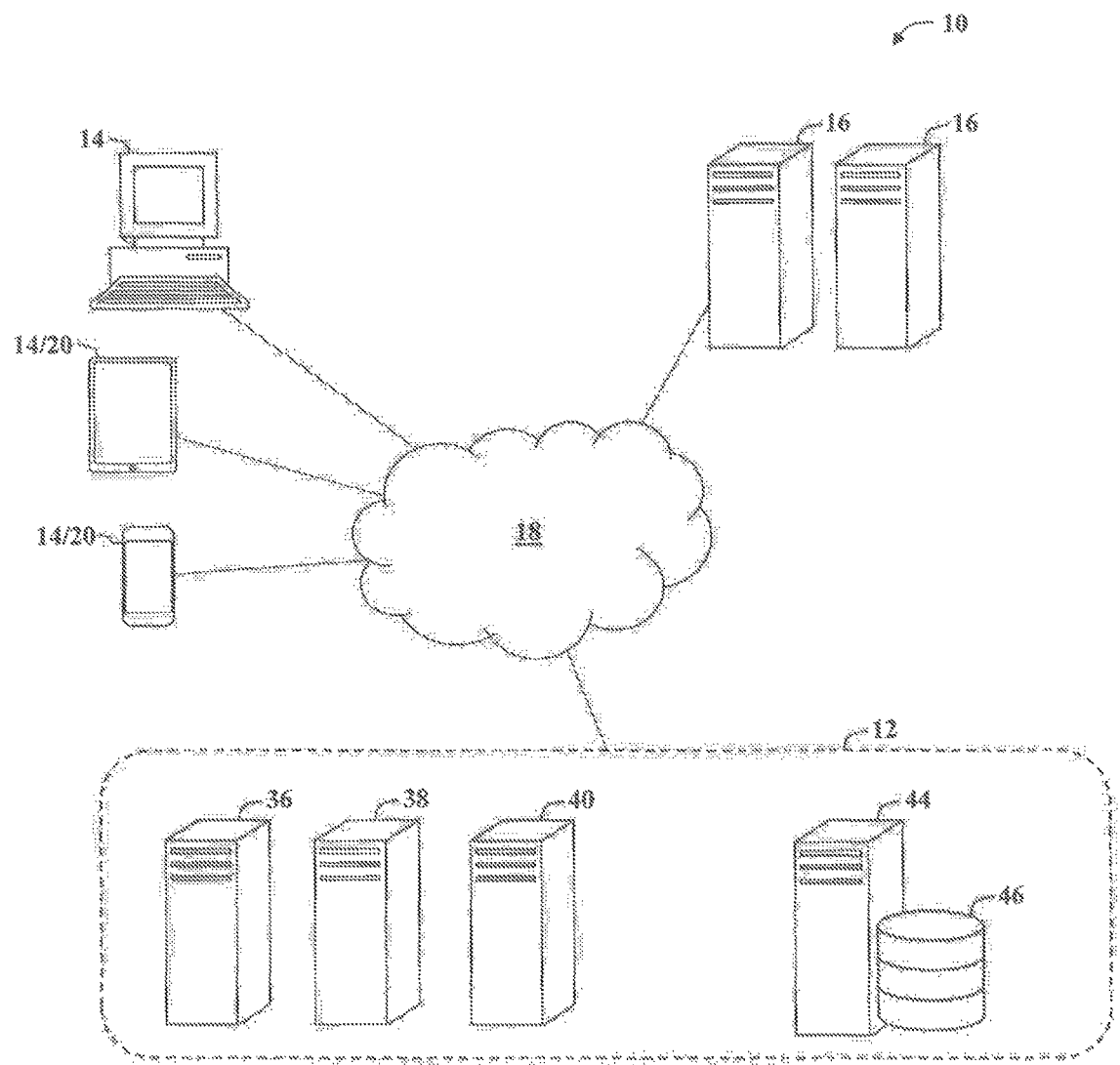
FIG. 1 is a schematic illustrating various aspects of a system, according to the present invention.

Corresponding reference characters indicate corresponding components throughout the several views of the drawings. Skilled artisans will appreciate that elements in the figures are illustrated for simplicity and clarity and have not necessarily been drawn to scale. For example, the dimensions of some of the elements in the figures may be exaggerated relative to other elements to help to improve understanding of various embodiments of the present invention. Also, common but well-understood elements that are useful or necessary in a commercially feasible embodiment are often not depicted in order to facilitate a less obstructed view of these various embodiments of the present invention.

DETAILED DESCRIPTION OF THE PREFERRED EMBODIMENT(S)

In the following description, numerous specific details are set forth in order to provide a thorough understanding of the present invention. It will be apparent, however, to one having ordinary skill in the art that the specific detail need not be employed to practice the present invention. In other instances, well-known materials or methods have not been described in detail in order to avoid obscuring the present invention.

Reference throughout this specification to "one embodiment", "an embodiment", "one example" or "an example" means that a particular feature, structure or characteristic described in connection with the embodiment or example is included in at least one embodiment of the present invention. Thus, appearances of the phrases "in one embodiment", "in an embodiment", "one example" or "an example" in various places throughout this specification are not necessarily all referring to the same embodiment or example. Furthermore, the particular features, structures or characteristics may be combined in any suitable combinations and/or sub-combinations in one or more embodiments or examples. In addition, it is appreciated that the figures provided herewith are for explanation purposes to persons ordinarily skilled in the art and that the drawings are not necessarily drawn to scale.

Embodiments in accordance with the present invention may be embodied as an apparatus, system, method, or computer program product. Accordingly, the present invention may take the form of an entirely hardware embodiment, an entirely software embodiment (including firmware, resident software, micro-code, etc.), or an embodiment combining software and hardware aspects that may all generally be referred to herein as a "module" or "system." Furthermore, the present invention may take the form of a computer program product embodied in any tangible media of expression having computer-usable program code embodied in the media.

Any combination of one or more computer-usable or computer-readable media (or medium) may be utilized. For example, a computer-readable media may include one or more of a portable computer diskette, a hard disk, a random access memory (RAM) device, a read-only memory (ROM) device, an erasable programmable read-only memory (EPROM or Flash memory) device, a portable compact disc read-only memory (CDROM), an optical storage device, and a magnetic storage device. Computer program code for carrying out operations of the present invention may be written in any combination of one or more programming languages.

Embodiments may also be implemented in cloud computing environments. In this description and the following claims, "cloud computing" may be defined as a model for enabling ubiquitous, convenient, on-demand network access to a shared pool of configurable computing resources (e.g., networks, servers, storage, applications, and services) that can be rapidly provisioned via virtualization and released with minimal management effort or service provider interaction, and then scaled accordingly. A cloud model can be composed of various characteristics (e.g., on-demand self-service, broad network access, resource pooling, rapid elasticity, measured service, etc.), service models (e.g., Software as a Service ("SaaS"), Platform as a Service ("PaaS"), Infrastructure as a Service ("IaaS"), and deployment models (e.g., private cloud, community cloud, public cloud, hybrid cloud, etc.).

The flowchart and block diagrams in the flow diagrams illustrate the architecture, functionality, and operation of possible implementations of systems, methods, and computer program products according to various embodiments of the present invention. In this regard, each block in the flowchart or block diagrams may represent a module, segment, or portion of code, which comprises one or more executable instructions for implementing the specified logical function(s). It will also be noted that each block of the block diagrams and/or flowchart illustrations, and combinations of blocks in the block diagrams and/or flowchart illustrations, may be implemented by special purpose hardware-based systems that perform the specified functions or acts, or combinations of special purpose hardware and computer instructions. These computer program instructions may also be stored in a computer-readable media that can direct a computer or other programmable data processing apparatus to function in a particular manner, such that the instructions stored in the computer-readable media produce an article of manufacture including instruction means which implement the function/act specified in the flowchart and/or block diagram block or blocks.

Several (or different) elements discussed below, and/or claimed, are described as being "coupled", "in communication with", or "configured to be in communication with". This terminology is intended to be non-limiting, and where appropriate, be interpreted to include without limitation, wired and wireless communication using any one or a plurality of a suitable protocols, as well as communication methods that are constantly maintained, are made on a periodic basis, and/or made or initiated on an as needed basis. The term "coupled" means any suitable communications link, including but not limited to the Internet, a LAN, a cellular network, or any suitable communications link. The communications link may include one or more of a wired and wireless connection and may be always connected, connected on a periodic basis, and/or connected on an as needed basis.

With reference to the FIGS. and in operation, the present invention provides a networked computer system 10, method, and computer product media that allows a mobile check-in for pharmacy customers at a pharmacy of a retail store and monitors the activities of said customers to provide notification of potential drug interactions to a user. Referring to FIG. 1, an exemplary environment in which the networked computer system 10 operates is illustrated. In general, the present invention describes a networked computer system 10 that allows mobile check-in with a pharmacy in a retail store that prioritizes at least one prescription fill order so that the prescription is filled so that the prescription is ready for pick up by the time the customer arrives at the pharmacy of the retail store. The present invention also describes a networked computer system 10 that monitors activities of pharmacy customers for potential drug interactions and provides pharmacy notifications to customers when potential drug interactions with existing pharmaceutical medications currently used by the customer is detected. Moreover, the networked computer system 10 is configured to communicate with a mobile device associated with the customer to provide push notifications to the mobile devices including messages about the potential drug interactions to the pharmacy customers. In addition, the system 10 may determine the location of the customer based on the geographic location of the corresponding mobile device and determine environmental conditions associated with the geographic area of the mobile device that may affect or require the use of the pharmaceutical medications being used by the customer. The system 10 may then transmit push notifications to the customer with information about current weather conditions in the area and reminders to use the appropriate pharmaceutical drug. The system 10 may also include a mobile computer application being stored on a mobile device associated with the pharmacy customer. The mobile application uses location and public API's to give warnings based on known conditions of the user. For example, in one embodiment, the pharmacy customer receives a push notification warning in the morning because the pollen count in their area is high and they are known users of an allergy medication. The system may also allow the pharmacy customer to identify additional users such as, for example, family, friends, and healthcare professionals, to receive similar notifications to provide the additional users with the information associated with the pharmacy customer.

The system 10 is configured to generate and store user pharmacy data records associated with pharmacy customers that includes information associated with pharmaceutical drugs being used by the customers. The system 10 also determines action events that are associated with the pharmaceutical drugs and generates and stores action records that includes information associated with actions to be performed by the system upon detecting activities being performed by the customer. In addition, the user pharmacy data records may include triggering events that are detected by the system to initiate the action events. The triggering events may include detecting purchases being made by the customers, requests being received by the customers, and/or customer selected calendar dates. The action events may include initiating data search operations to search e-receipt data to determine potential drug interactions and/or provide notifications to the customer of the potential drug interaction via the customer's mobile device.

By generating action event records associated with customer activities that include triggering events that trigger corresponding system actions, the system 10 improves the speed and functionality of known computing systems by reducing the amount of computing time required to monitor customer activity, thus reducing the computing resources required to generate and display relevant pharmacy messages to pharmacy customers.

For clarity in discussing the various functions of the system 10, multiple computers and/or servers are discussed as performing different functions. These different computers (or servers) may, however, be implemented in multiple different ways such as modules within a single computer, as nodes of a computer system, etc. . . . The functions performed by the system 10 (or nodes or modules) may be centralized or distributed in any suitable manner across the system 10 and its components, regardless of the location of specific hardware. Furthermore, specific components of the system 10 may be referenced using functional terminology in their names. The function terminology is used solely for purposes of naming convention and to distinguish one element from another in the following discussion. Unless otherwise specified, the name of an element conveys no specific functionality to the element or component.

In the illustrated embodiment, the system 10 includes a server system 12 that is coupled in communication with one or more user computing devices 14 and one or more 3rd party entity server systems 16 via a communications network 18. The communications network 18 may be any suitable connection, including the Internet, file transfer protocol (FTP), an Intranet, LAN, a virtual private network (VPN), cellular networks, etc. . . . , and may utilize any suitable or combination of technologies including, but not limited to wired and wireless connections, always on connections, connections made periodically, and connections made as needed.

The user computing device 14 may include any suitable device that enables a user to access and communicate with the system 10 including sending and/or receiving information to and from the system 10 and displaying information received from the system 10 to a user. For example, in one embodiment, the user computing device 14 may include, but is not limited to, a desktop computer, a laptop or notebook computer, a tablet computer, smartphone/tablet computer hybrid, a personal data assistant, a handheld mobile device including a cellular telephone, and the like. The user computing device 14, as well as any other connected computer systems and their components included in the system 10, can create message related data and exchange message related data (e.g., near field communication ("NFC") payloads, Bluetooth packets, Internet Protocol ("IP") datagrams and other higher layer protocols that utilize IP datagrams, such as, Transmission Control Protocol ("TCP"), Hypertext Transfer Protocol ("HTTP"), Simple Mail Transfer Protocol ("SMTP"), etc.) over the network.

Figure 3:
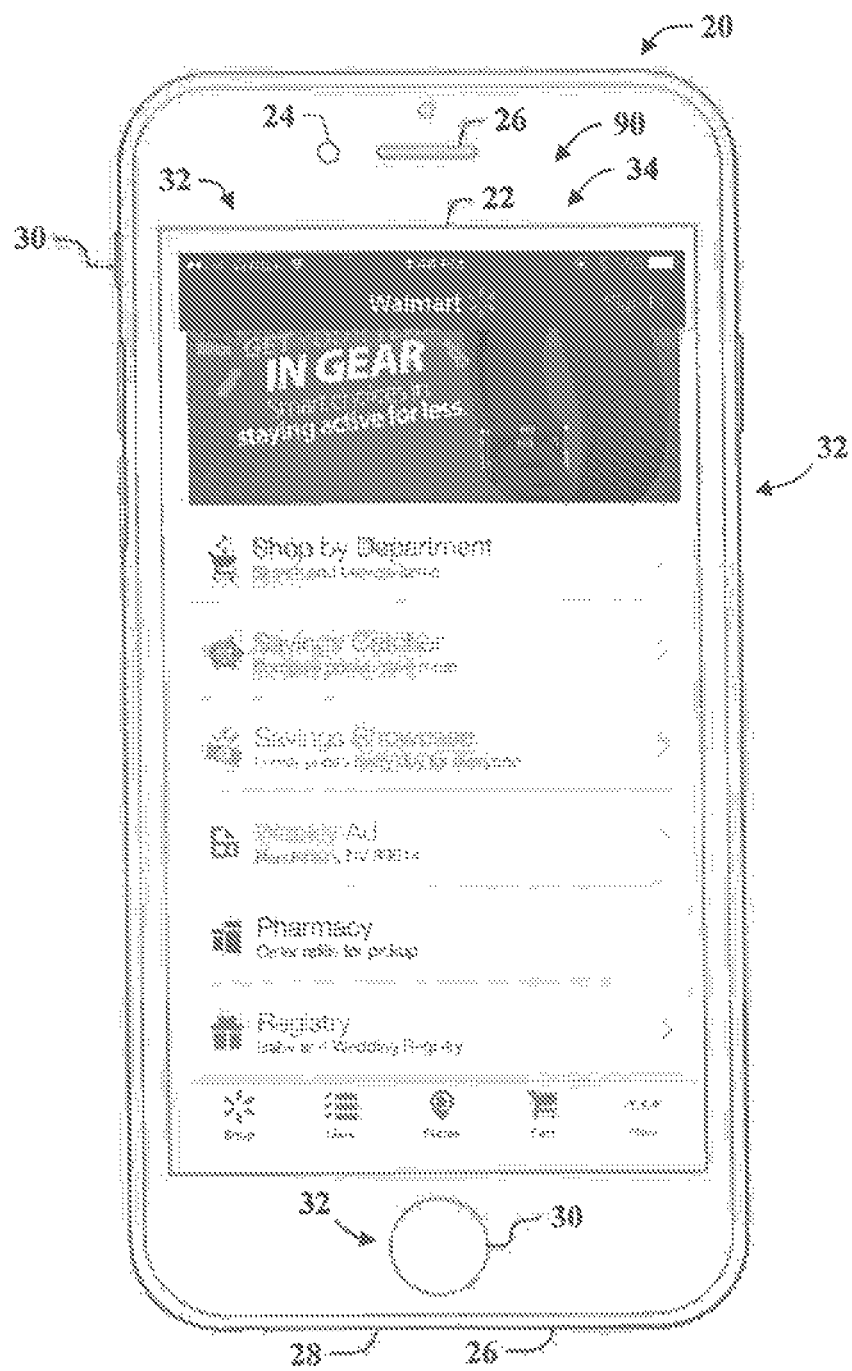
FIG. 3 is an illustration of an exemplary screenshot from the system of FIG. 1, according to an embodiment of the present invention.

In one embodiment, the user computing device 14 includes a mobile computing device 20 (shown in FIG. 3) such as, for example, a smartphone such as an iPhone™. The mobile computing device 20 includes a processor coupled to a memory device, and a database for storing various programs and data for use in operating the mobile computing device 20. The mobile computing device 20 may also include a touchscreen display device 22, one or more video image cameras 24, one or more speakers 26, a microphone 28, at least one input button 30, and one or more sensors 32 including, but not limited to, a touch ID fingerprint sensor coupled to the input button 30, a barometer, a three-axis gyro, an accelerometer, proximity sensor, and an ambient light sensor. In addition, the mobile computing device 20 may also include a Wi-Fi antenna, a cellular network antenna, a Bluetooth' communications device, assisted GPS and GLONASS, a digital compass, and an iBeacon microlocation device.

The GPS is a device that determines a location of the mobile computing device 20 by communicating with a plurality of GPS satellites. The GPS can perform known triangulation techniques to determine the GPS coordinates of the mobile computing device 20. It should be appreciated that while a GPS is shown, any other suitable component for determining the location of the mobile computing device 20 can be implemented.

In the illustrated embodiment, the mobile computing device 20 includes a web browser program stored in the memory device. The processor executes the web browser program to display web pages on the touchscreen display device 22 that includes information received from the server system 12 to enable a user to interact with and operate the server system 12. In addition, the mobile computing device 20 may be programmed to store and execute computer program applications that display user interfaces 34 (shown in FIGS. 3 and 6-9) on the touchscreen display device 22 that allows the user to access the server system 12 to retrieve and store information within the server system 12 as well as interact with and operate the server system 12. In addition, in one embodiment, the system 10 may install one or more mobile computer application programs in the memory device of the mobile computing device 20. When initiated by the processor of the mobile computing device 20, the mobile computer application program causes the processor of the mobile computing device 20 to perform some or all of the functions of the server system 12.

The 3rd party entity server systems 16 include information and data associated with environmental condition associated with various locations. For example, in one embodiment, the 3rd party entity server systems 16 may include environmental information associated with weather conditions for various geographical locations. The environmental information may include, for example, temperature, cloud conditions, wind conditions, air conditions such as dust and/or smog levels, UV data, barometric pressure, humidity, precipitation data, allergy information such as type of pollen and pollen counts, and/or any suitable environmental information associated with geographic locations. In addition, the environmental information may include historic weather and/or allergen conditions, and/or predictive weather and/or allergen conditions.

In the illustrated embodiment of FIG. 1, the server system 12 includes a website hosting server 36, e-receipts server 38, a pharmacy account server 40, a database server 44, and a database 46. The database server 44 includes a memory device that is connected to the database 46 to retrieve and store information contained in the database 46. The database 46 contains information on a variety of matters, such as, for example, web pages associated with one or more websites, search queries, pharmaceutical drug information, food-drug interaction data, drug-drug interaction data, prescription fill order information, prescription refill information, entity authentication information, customer pharmacy account information, product records, e-receipt data, action events, action trigger conditions, notification messages, mobile device identifies, mobile device application program interfaces (APIs), and/or any suitable information that enables the system 10 to function as described herein. In one embodiment, some or all of the information contained in the database 46 may also be stored in the database of the mobile computing device 20.

Figure 4:
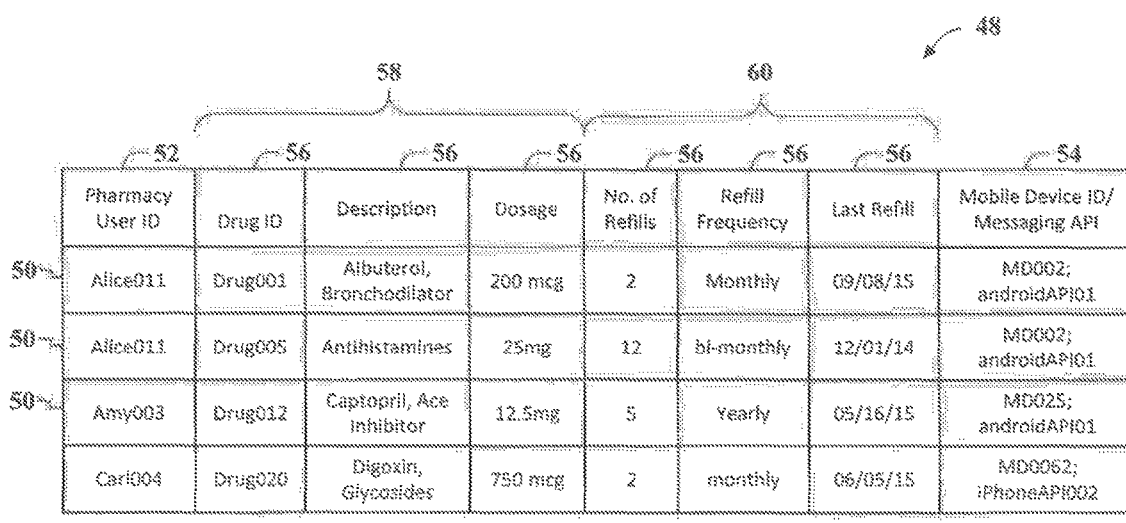
FIG. 4 is an illustration of exemplary database records generated by the system of FIG. 1, according to an embodiment of the present invention.

In the illustrated embodiment, the database 46 includes a pharmacy account list 48 (shown in FIG. 4) that includes a plurality of user pharmacy account records 50. Each user pharmacy account record 50 is associated with a corresponding pharmacy customer and includes user identification information 52 associated with the pharmacy customer and pharmaceutical drug data associated with pharmaceutical drugs prescribed to and/or purchased by the corresponding pharmacy customer. The user identification information 52 includes user identifying data such as, for example, a unique user ID and/or password. The user identification information 52 may also include user contact information such as, for example, a phone number, an email, and/or a mobile device data 54 associated with a mobile computing device 20 associated with the corresponding pharmacy customer. For example, the mobile device data 54 may include, but is not limited to, a unique mobile device ID, operating system, phone number, IP address, mobile device API, and/or any suitable information that enables the system 10 to communicate with the corresponding mobile computing device 20.

In the illustrated embodiment, each user pharmacy account record 50 includes a plurality of data categories 56 associated with the pharmaceutical drugs prescribed to and/or purchase by the pharmacy customer. The data categories 56 includes information associated with the pharmaceutical drugs and activities associated with the pharmacy customers. For example, in one embodiment, each user pharmacy account record 50 may include a first data group 58 including data categories 56 including information associated with a corresponding pharmaceutical drug and a second data group 60 including data categories including information indicating pharmacy customer activities associated with the corresponding pharmaceutical drug. The first data group 58 may include data categories 56 including information indicating a unique drug ID associated with the pharmaceutical drug, pharmaceutical drug name, pharmaceutical drug description, drug category, prescribed use information, dosage information, number of refills, side effects and/or any suitable information associated with the corresponding pharmaceutical drug. The second data group 60 may include data categories 56 including information indicating a prescription fill order, number of prescription refills remaining, a prescription refill frequency, a date and/or time of a prescription fill order, a date and/or time of the last prescription refill purchase, purchase date, and/or prescription expiration, and/or any suitable information associated with pharmacy customer activity.

In one embodiment, the database 46 also includes a drug action list that includes a plurality of pharmaceutical drug action records. Each pharmaceutical drug action record includes pharmaceutical drug information and corresponding action records. The drug information includes information associated with pharmaceutical drugs such as, for example, drug categories 60 and drug identifiers 62 associated with the corresponding drug categories. Each action record 56 is associated with one or more drug identifiers 62 and includes and action record ID and information associated with actions and/or operations that may be initiated by the system 10.

In one embodiment, the database 46 may also include an action event list that includes a plurality of action records. Each action record may include triggering event data indicating a triggering event and action event data associated with an action and/or operation that may be initiated by the system 10. Action event data includes information and data including, but are not limited to, action event descriptions, an action record ID, and/or action rule description. The action event description may include data associated with food-drug interactions, drug-drug interactions, and/or use reminders. The action rule description includes data that enables the system to perform particular actions and operations associated with the corresponding action record. For example, in one embodiment, the action rule description may include data that enables the system 10 to initiate a data search operation that searches e-receipt data for purchases the include foods and/or drugs that may interact with the corresponding pharmaceutical drug, and/or perform a search for weather data that may trigger medication reminder notifications. The triggering event data includes data associated with a triggering event that includes an event or occurrence that may be detected by the system 10. Event triggers may include, but are not limited to, requests and/or signals received by a user computing device 14, a consumer product purchase, a pharmaceutical drug purchase, calendar events such as, for example, a day of the week, month, and/or year, a time of day, and/or any suitable triggering event that enable the system 10 to perform as described herein.

The database 46 may also include a user action event list that include a plurality of user event action records that are associated with a plurality of pharmacy customers. Each user event action record includes a user identification information 52 associated with the corresponding pharmacy customer, a drug identifier 52 indicating pharmaceutical drugs associated with the corresponding user identification information 52, and an action record associated with each corresponding pharmaceutical drug. In addition, the user event action record may also include mobile device data 54 including data and information associated with a mobile computing device 20 associated with the corresponding user identification information and/or API information associated with the corresponding mobile computing device 20. In one embodiment, the mobile device data 54 may also include contact information such as, for example, emails and/or text and phone numbers, associated with friends, relatives, and/or healthcare professionals associated with the pharmacy customer. The pharmacy customer may identify one or more additional users that may receive notifications generated by the pharmacy account server 40 and include contact information associated with the identified additional users in the mobile device data 54.

In one embodiment, the database 46 may include a drug interaction search term list that includes information and search terms for use in performing data search operations. The drug interaction search term list includes a plurality of data search records. Each data search record includes information associated with a corresponding action event. For example, the information included in the data search record may include and action ID associated with a corresponding action event, associated drug information, food-interaction search terms, and/or drug interaction search terms.

Figure 5:
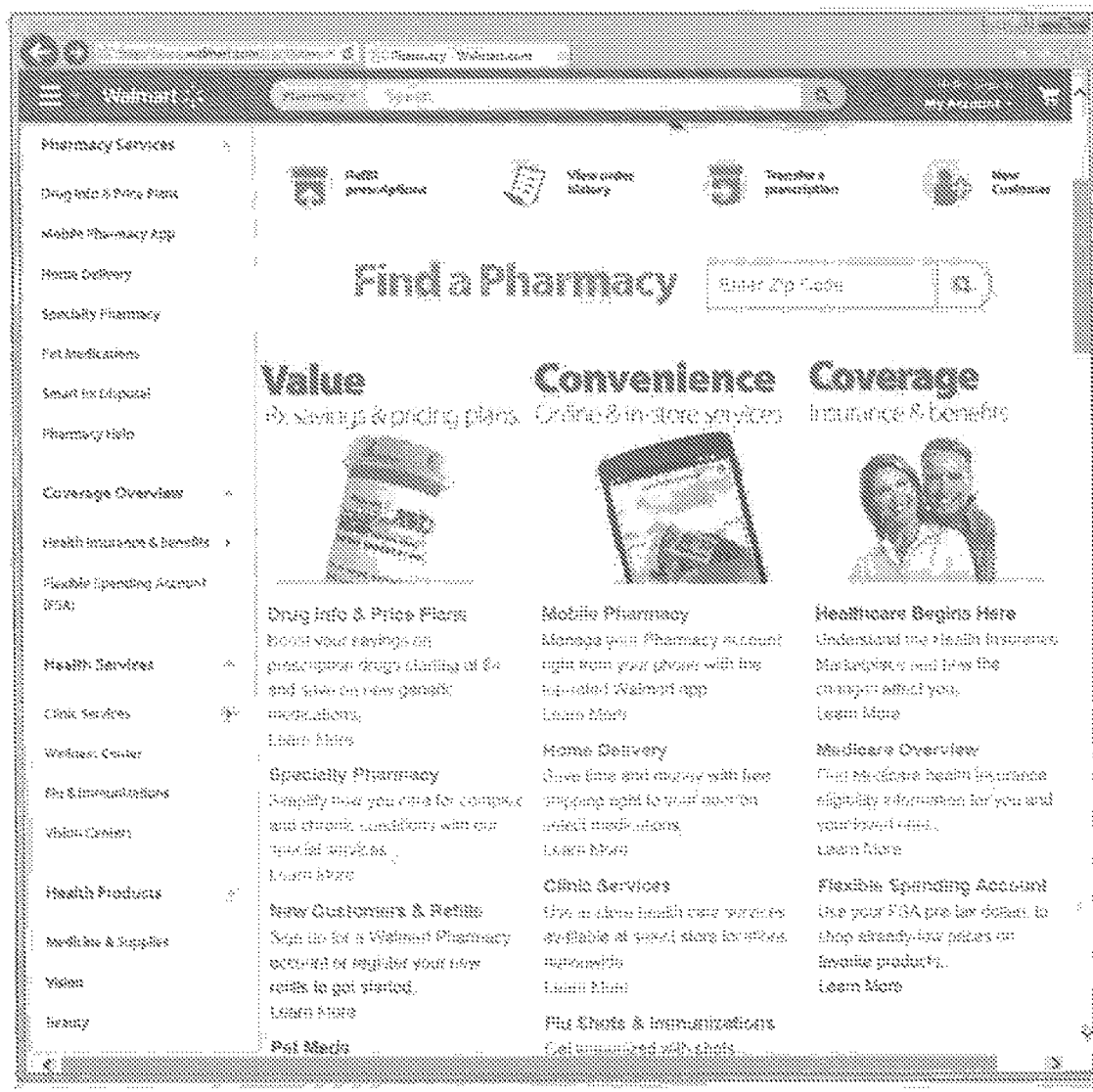
FIG. 5 is an illustration of an exemplary screenshot from the system of FIG. 1, according to an embodiment of the present invention.
Figure 6:
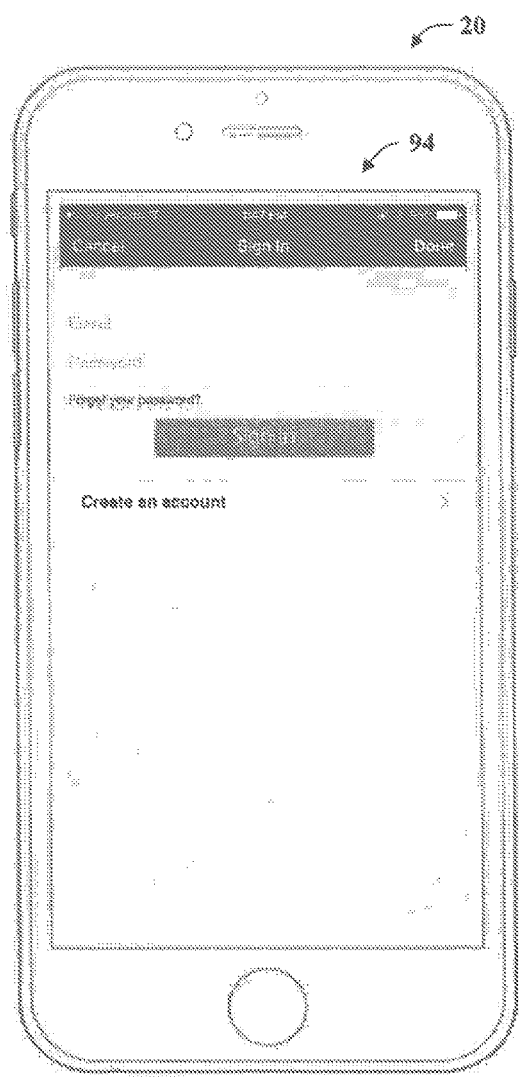
FIGS. 6-9 are illustrations of exemplary screenshots from the system of FIG. 1, according to an embodiment of the present invention.
Figure 7:
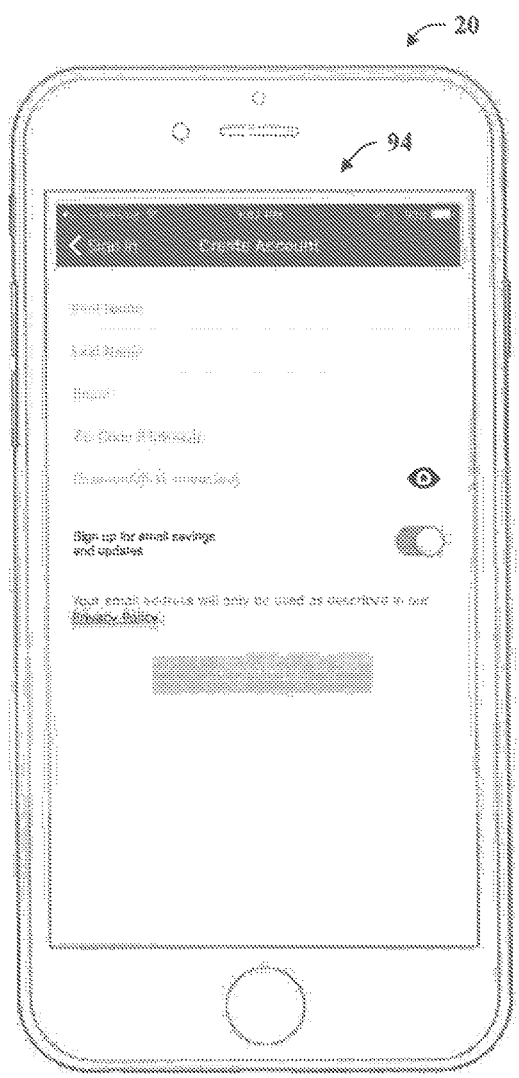
Figure 8:
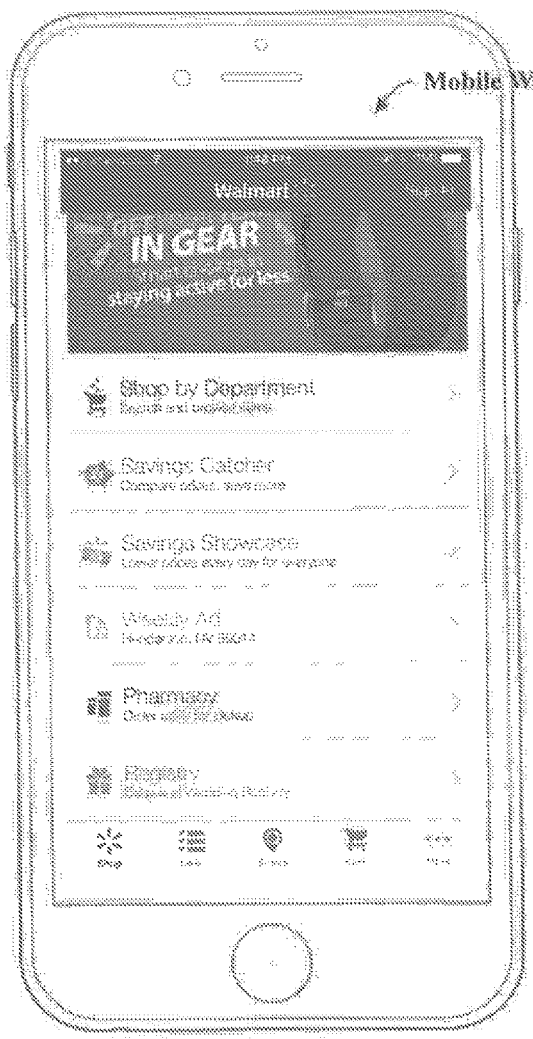
Figure 9:
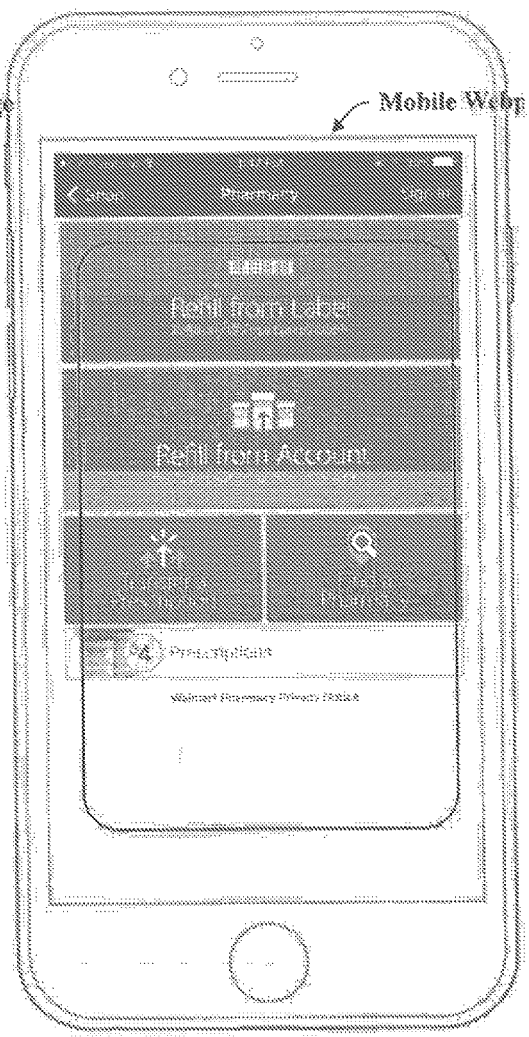

The website hosting server 36 is configured to host a website 86 that is accessible by a user via one or more user computing devices 14. The website hosting server 36 retrieves and stores web pages 88 (shown in FIG. 5) associated with one or more websites 86 in response to requests received by the user via the user computing device 14 to allow users to interact with the website and search and/or purchase products such as, for example, goods and/or services via the website. In one embodiment, the website hosting server 36 is configured to generate and display web pages 88 associated with the website in response to requests being received from consumers via corresponding web browsers that are displayed on the user computing devices 14. In addition, the website hosting server 36 may be configured to generate and display a mobile webpage 90 (shown in FIG. 6-9) that is displayed on one or more mobile computing devices 20. For example, in one embodiment, the website hosting server 36 may display a pharmacy webpage 92 (shown in FIGS. 6-9) in response to receiving a user request that allows a user to access a corresponding user pharmacy account record 50, input product search requests including search criteria including one or more search terms, purchase pharmaceutical drugs, request prescription fills, request prescription refills, request pharmacist consultations, schedule pharmacy and/or medical clinic appointments, and the like.

The website hosting server 36 may allow customers to login and access corresponding customer pharmacy accounts including account information such as, for example, previous purchases, pending prescription fill orders, pending prescription refills, and/or pharmaceutical drug information. For example, the website hosting server 36 may display a login page 94 (shown in FIGS. 6-7), receive a unique customer ID such as, for example, a username and/or password, and identify the customer account associated with the unique customer ID to enable the identified customer to access information and/or features associated with the corresponding customer pharmacy account. In addition, the website hosting server 36 may transmit search requests to the search engine server and/or the pharmacy account server 40 for use in generating search data and/or pharmacy information in response to the user's search request. The website hosting server 36 may also receive one or more product lists from the search engine server and/or the pharmacy account server 40 that includes information associated with products that are selected based on the user's search criteria. The website hosting server 36 may also display a search results webpage to display the product lists to the user and to allow the user to select one or more of the displayed products for purchase.

The e-receipts server 38 receives and stores information associated with consumer retail purchases in the database 46 and is programmed to generate and store electronic receipt data associated with the consumer retail purchases. In addition, the e-receipts server 38 may be programmed to transmit signals indicating pharmacy customer purchases to the pharmacy account server 40. In one embodiment, the e-receipts server 38 may communicate with a plurality of point-of-sale (POS) systems as well as other computer systems at each of the one or more physical store locations (e.g., on an internal corporate network) to facilitate business operations for the corresponding entity. The e-receipts server 38 is programed to receive application identifiers and digital receipt data, including item data for one or more purchased items, from POS systems at various different store locations, and generate and store digital receipts from received receipt data. Generating digital receipts can include item data for items included in corresponding digital receipt data (but potentially in a different format, for example, a format deliverable to mobile devices). Formulated digital receipts can also contain other data related to a transaction, such as, for example, the payment method used for the transaction, coupons, surveys, etc. For example, a pharmacy customer may purchase a pharmaceutical drug using a POS system at a store location. The e-receipts server 38 may generate e-receipt data indicating the purchase and transmit the e-receipt data to the pharmacy account server 40 for use in modifying a corresponding user pharmacy account record 50 to include information associated with the pharmaceutical drug purchase.

In an embodiment, the search engine server is configured to receive a search request from the website hosting server 36 and/or the pharmacy account server 40 including one or more search terms, and generate search data including a plurality of records as a function of the search terms. For example, in one embodiment, the search engine server may initiate a search algorithm based on a Boolean model to search pharmacy records and/or search terms contained in the drug interaction search term list contained in the database 46 based search terms received from the user and/or received from the pharmacy account server 40. The search engine server may generate search data including pharmaceutical drugs matching the search criteria, generate a relevance score associated with each pharmaceutical drug included in the search data, and transmit the relevancy score to the pharmacy account server 40. In one embodiment, the relevance score may be determined based on statistical information, including, but not limited to the number of records in the database, the frequency in which the search terms appear in the database, and the frequency in which the search term appears in the pharmaceutical drug record. The relevance of a returned search record may be determined based on the corresponding relevance score and the relevance scores of the other pharmaceutical drugs records in the search data, wherein records having a higher relevance scores are more relevant to the search criteria.

In an embodiment, the pharmacy account server 40 is programmed to monitor activities associated with prescription drugs being used by pharmacy customers. For example, in one embodiment, the pharmacy account server 40 is configured to monitor consumer product purchases being made by pharmacy customers in order to determine potential drug interactions and/or food interactions with currently prescribed prescriptions drugs being used by the corresponding pharmacy customers. In addition, the pharmacy account server 40 is programmed to detect the occurrence of triggering events associated with pharmaceutical drugs being used by pharmacy customers and transmit pharmacy notification messages to the customers to provide information and notifications of the potential interactions. In addition, the pharmacy account server 40 may also be programmed to monitor environmental conditions associated the geographic locations of the pharmacy customers for use in generating pharmacy notification messages that include reminders for taking prescription allergy medication.

In an embodiment, the pharmacy account server 40 is programmed to receive a signal indicating a purchase of a pharmaceutical drug by a pharmacy customer. The signal may include an indication of a purchase being made by the customer and be received from the e-receipts server 38 and/or include a request to fill a prescription received from the pharmacy website. In addition, the signal may include a pharmaceutical drug ID and a user ID. In one embodiment, the pharmacy account server 40 may access the pharmacy account list 48 being stored in the database an determine the user pharmacy account records 50 that is associated with the received user ID, determine one or more pharmaceutical drugs associated with the user ID, and determine the pharmaceutical drug ID associated with each corresponding pharmaceutical drug.

In an embodiment, the pharmacy account server 40 determines a drug category associated with each drug ID, and accesses the drug action list included in the database 46 to determine a drug action record associated with each corresponding pharmaceutical drug as a function of the determined drug category and the corresponding drug ID. The pharmacy account server 40 determines the action ID associated with the drug action record and accesses the action event list to obtain the corresponding action record including the triggering event data and action event data associated with the action ID. The pharmacy account server 40 may then generate and store a user event action record associated with the user ID including the information contained in the action record and information associated with a pharmacy notification message associated with the action record.

For example, in one embodiment, the pharmacy account server 40 may receive a signal indicating a purchase of a pharmaceutical drug including a pharmaceutical drug ID and a user ID, access the drug action list including pharmaceutical drug action records being stored in the database 46, select a pharmaceutical drug action record as a function of the received pharmaceutical drug ID, determine the action event data associated with the selected pharmaceutical drug action record, and generate a user pharmacy account record associated with the received user ID including the determined action event data associated with the selected pharmaceutical drug action record. The corresponding user pharmacy account record includes information that allows the pharmacy account server 40 to monitor purchases being made by the pharmacy customer to facilitate notifying the pharmacy customer of potential food and drug interactions with current prescription medications.

In an embodiment, the pharmacy account server 40 receives a request to display a pharmacy notification message to a user via a user computing device 14. For example, the pharmacy notification message may include information associated with a medication reminder and/or a drug interaction. In one embodiment, the pharmacy account server 40 may receive a request to display the pharmacy notification message on a mobile computing device 20. In an embodiment, the request includes a corresponding user ID. Upon receiving the request, the pharmacy account server 40 accesses the database 46 and identifies a user pharmacy account record 50 associated with the received user ID. The pharmacy account server 40 is programmed to determine a pharmaceutical drug included in the identified user pharmacy account record 50 and determines an action record associated with the determined pharmaceutical drug. The pharmacy account server 40 also determines the triggering event data and the action event data corresponding to the action record.

The pharmacy account server 40 also detects an occurrence of a triggering event as a function of the triggering event data, and initiates a data search operation associated with the corresponding action event data upon detecting the occurrence of the triggering event. The pharmacy account server 40 then determines an outcome of the data search operation and generates a pharmacy notification message as a function of the outcome of the data search operation. The pharmacy account server 40 then generates and transmits a signal including the pharmacy notification message to the mobile computing device 20 to cause the mobile computing device 20 to display the pharmacy notification message on the mobile computing device 20.

In one embodiment, the pharmacy account server 40 may determine the triggering event to include an indication of a purchase of consumer products by the user. In addition, the triggering event may include a purchase of pharmaceutical drugs by the user and/or a request to fill a prescription for pharmaceutical drugs being submitted through the website. For example, the pharmacy account server 40 may receive a signal from the e-receipts server 38 indicating a purchase being made by a customer. The signal may include a user ID associated with the customer. In addition, the pharmacy account server 40 may receive electronic receipt data including product information associated with consumer products purchased by the user from the e-receipts server 38. In one embodiment, the pharmacy account server may retrieve the electronic receipt data from the database 46 using the corresponding user ID.

Upon receiving the electronic receipt data, the pharmacy account server 40 initiates the data search operation including transmitting the electronic receipt data to the search engine server for use in conducted the data search operation using the electronic receipt data. In one embodiment, during the data search operation, the pharmacy account server 40 generates search terms associated with the pharmaceutical drug included in the identified user pharmacy account record 50 and transmits the search terms to the search engine server. In one embodiment, the pharmacy account server 40 is programmed to access the drug interaction search term list being stored in the database 46 to determine search terms associated with the determined pharmaceutical drug included in the associated user pharmacy account record 50, and transmits the determined search terms to the search engine server. The search engine server conducts a data search operation to review the electronic receipt data to determine if at least one consumer product included in the electronic receipt data includes product information matching the determined search terms. In one embodiment, the search engine server transmits the matching search terms to the pharmacy account server 40 for use in generating the pharmacy notification message.

For example, the pharmacy account server 40 may transmit the notification message upon determining at least one consumer product includes product information matching one or more of the determined search terms associated with the determined pharmaceutical drug. In one embodiment, search terms may be associated with other pharmaceutical drugs. The pharmacy account server 40 may select a notification message indicating a potential drug-drug interaction if the search engine server returns a matching drug purchased by the consumer. In addition, in one embodiment, the search terms may be associated with food products. The pharmacy account server 40 may select a notification message indicating a potential food-drug interaction if the search engine server returns a matching food purchased by the consumer.

In one embodiment, the triggering event may include a request for allergy information being received from a customer's mobile computing device 20. Upon receiving a request for allergy information, the pharmacy account server 40 may request and receive weather data including location data and associated allergen data from the 3rd party entity server systems 16. The pharmacy account server 40 may initiate the data search operation including, receiving location data from the corresponding mobile computing device 20, determine a current location of the mobile computing device 20, review the received weather data to identify location data matching the current location of the mobile computing device, and determine an allergen count value as a function of the allergen data associated with the identified location data. For example, the pharmacy account server 40 may generate a pollen count value as a function of the allergen data received from the 3rd party entity server systems 16. In an embodiment, the pharmacy account server 40 determines if the allergen count associated with the location of the mobile computing device 20 is equal to, or greater than, a predefined allergen count, and generates and transmits a pharmacy notification message upon determining the determined allergen count value to be greater than, or equal to, the predefined allergen count value.

In one embodiment, the pharmacy account server 40 may allow the user to establish a calendar event as the triggering event to allow the system 10 to perform a daily, weekly, and or monthly review of environmental allergies. In addition, the user may establish triggering events associated with food-drug interactions. For example, in one embodiment, the pharmacy account server 40 may display a notification trigger webpage to allow the user to establish triggering events associated with the corresponding user pharmacy account record 50. The user may establish calendared reminders to prompt the pharmacy account server 40 to conduct data search operations upon the occurrence of user defined events. In addition, the pharmacy account server 40 may allow the user to op-out of push notifications and not receive notifications generated by the system 10.

In one embodiment, the pharmacy account server 40 may generate the notification message including a hyperlink including a pharmaceutical drug ID to allow the user to cause the system 10 to display additional information associated with the corresponding pharmaceutical drug. For example, the pharmacy account server 40 may receive a signal from the mobile computing device 20 indicating that the user has accessed the hyperlink, access the list of pharmaceutical drug records stored in the database 46 with each pharmaceutical drug record associated with a pharmaceutical drug and including a corresponding pharmaceutical drug ID and corresponding pharmaceutical drug data information associated including information associated with the corresponding pharmaceutical drug. The pharmacy account server 40 then retrieves the pharmaceutical drug record corresponding to the received pharmaceutical drug ID and generates and displays an information webpage on the mobile computing device 20 including drug-related information included in the retrieved pharmaceutical drug record.

The e-receipts server 38 is programmed to receive application identifiers and digital receipt data, including item data for one or more purchased items, from POS systems at various different store locations, and generate and store digital receipts from received receipt data. Generating digital receipts can include item data for items included in corresponding digital receipt data (but potentially in a different format, for example, a format deliverable to mobile devices). In the illustrated embodiment, 20 associated with the pharmacy customer. The request may also be received from the pharmacy server 42 may also transmit a validation failure message to the pharmacy account server 40 if the authentication server 42 cannot validate the identity of the entity server system 16.

In one embodiment, the pharmacy account server 40 may also access the user pharmacy account record 50 associated with the user ID, retrieve contact information associated with the corresponding pharmacy customer, and transmit a verification message to the pharmacy customer based on the retrieved contact information. The verification message may include a verification hyperlink including verification data that allows the pharmacy customer to access the hyperlink and transmit a verification signal to the pharmacy account server 40. For example, in one embodiment, the user pharmacy account record 50 may include an email address and/or a phone number associated with a phone capable of received SMS text messages. The pharmacy account server 40 may generate the verification message including an email message and/or SMS text message and transmit the email message and/or SMS text message including the verification hyperlink 102 to the pharmacy customer.

Figure 2:
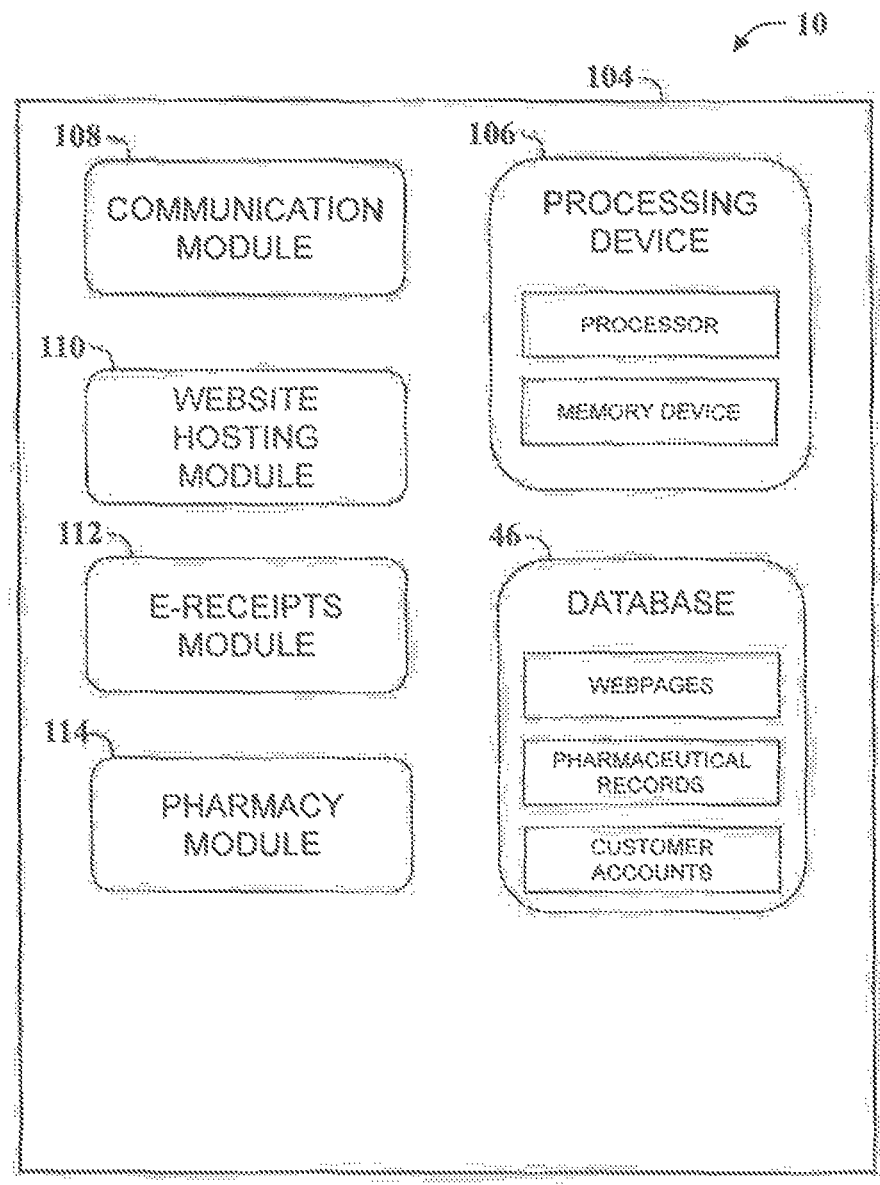
FIG. 2 is a schematic illustrating example components of a server computer that may be used with the system shown in FIG. 1, according to an embodiment of the present invention.

Referring to FIG. 2, in one embodiment, the system 10 may include a system server 104 that is configured to perform the functions of the website hosting server 36, the e-receipts server 38, the pharmacy account server 40, and the database server 44. In the illustrated embodiment, the system server 104 includes a processing device 106 and the database 46.

The processing device 106 executes various programs, and thereby controls components of the system server 104 according to user instructions received from the user computing device 14. The processing device 106 may include memory, e.g., read only memory (ROM) and random access memory (RAM), storing processor-executable instructions and one or more processors that execute the processor-executable instructions. In embodiments where the processing device 106 includes two or more processors, the processors can operate in a parallel or distributed manner. In an example, the processing device 106 may execute a communications module 108, a website hosting module 110, an e-receipts module 112, and a pharmacy account module 114.

The processing device 106 may also include a memory device for storing programs and information in the database 46, and retrieving information from the database 46 that is used by the processor to perform various functions described herein. The memory device may include, but is not limited to, a hard disc drive, an optical disc drive, and/or a flash memory drive. Further, the memory device may be distributed and located at multiple locations.

The communications module 108 retrieves various data and information from the database 46 and sends information to the user computing device 14 via the communications network 18 to enable the user to access and interact with the system 10. In one embodiment, the communications module 108 displays various images on a graphical interface of the user computing device 14 preferably by using computer graphics and image data stored in the database 46 including, but not limited to, web pages, pharmacy records, pharmacy notification messages, product lists, and/or any suitable information and/or images that enable the system 10 to function as described herein.

The website hosting module 110 may be programmed to perform some or all of the functions of the website hosting server 36 including hosting various web pages associated with one or more websites that are stored in the database 46 and that are accessible to the user via the user computing device 14. The website hosting module 110 may be programmed to generate and display web pages associated with a website in response to requests being received from users via corresponding web browsers.

The e-receipts module 112 may be programmed to perform some or all of the functions of the e-receipts server 38 including generating, receiving, and storing e-receipt data in the database 46 and detecting purchases being made by the pharmacy customers.

The search engine module may be programmed to perform some or all of the functions of the search engine server including generating and storing search data in response to the user's product search request and/or pharmacy account module search requests. In addition, the search engine module may also be programmed to generate a relevance score associated with each of the records included in the search data.

The pharmacy account module may be programmed to perform some or all of the functions of the pharmacy account server 40 including monitoring activities associated with pharmacy customers including consumer purchase and/or prescription refill requests and generate notification messages associated with the monitored activities. In addition, the pharmacy account module may be programmed to perform calendared tasks requested by the user including scheduled review of environmental information associated with a geographic location of a mobile computing device 20.

The pharmacy account module 114 may be programmed to perform some or all of the functions of the pharmacy account server 40 including monitoring activities associated with pharmacy customers including consumer purchase and/or prescription fill orders or requests, prescription refill orders or requests, generate notification messages associated with the monitored activities, transmit and received data from 3rd party entity server systems 16, and executing verification and authorization operations.

In one embodiment, the system 10 may access the corresponding user pharmacy account records 50 to determine a messaging API associated with an operating system of the mobile computing device 20 and generates the notification message as a function of the retrieved messaging API to enable the mobile computing device 20 to display the received message. In one embodiment, each user account record includes information associated with the mobile computing device 20 including a unique mobile ID and message API. In another embodiment, the user pharmacy account records 50 may include a message preferences, such as, for example, an email, text message, push messaging, automated phone call, and the like. The pharmacy account server 40 identifies the messaging preference associated with the user pharmacy account records 50 and generates the notification message based on the message preference. In addition, the pharmacy account server 40 may also access the mobile device data 54 to identify contact information associated with additional users associated with the pharmacy customer and generate and transmit similar notifications including the information associated with the pharmacy customer to the additional users designated by the pharmacy customer and identified in the mobile device data 54.

In general, the system 10 is configured to generate pharmacy user account records that include action event data that enable the system to monitor activities of pharmacy customers. For example, the system 10 may monitor the activities of pharmacy customers for potential drug interactions and provide pharmacy notifications to customers when potential drug interactions with existing pharmaceutical medications currently used by the customer is detected. Moreover, the system 10 is configured to provide push notifications to the mobile devices associated with the pharmacy customers to provide information about potential drug interactions and allow the customers to interact with an operate the system 10. By generating user pharmacy account records that include action event records associated with customer activities including triggering events, the system 10 improves the speed and functionality of known computing systems by reducing the amount of computing time required to monitor customer activity, thus reducing the computing resources required to generate and display relevant pharmacy messages to pharmacy customers.

Other features of the system 10 can be found in the following commonly owned US Patent Applications, which are hereby incorporated by reference: U.S. patent application Ser. No. 15/009,327, filed on Jan. 28, 2016; U.S. patent application Ser. No. 15/009,374, filed on Jan. 28, 2016; U.S. patent application Ser. No. 15/009,417, filed on Jan. 28, 2016; U.S. patent application Ser. No. 15/009,561, filed on Jan. 28, 2016; U.S. patent application Ser. No. 15/009,436, filed on Jan. 28, 2016; U.S. patent application Ser. No. 15/009,654, filed on Jan. 28, 2016; U.S. patent application Ser. No. 15/009,583, filed on Jan. 28, 2016; U.S. patent application Ser. No. 15/009,454, filed on Jan. 28, 2016; U.S. patent application Ser. No. 15/009,598, filed on Jan. 28, 2016; U.S. patent application Ser. No. 15/009,634, filed on Jan. 28, 2016; and, U.S. patent application Ser. No. 15/009,644, filed on Jan. 28, 2016.

Figure 10:
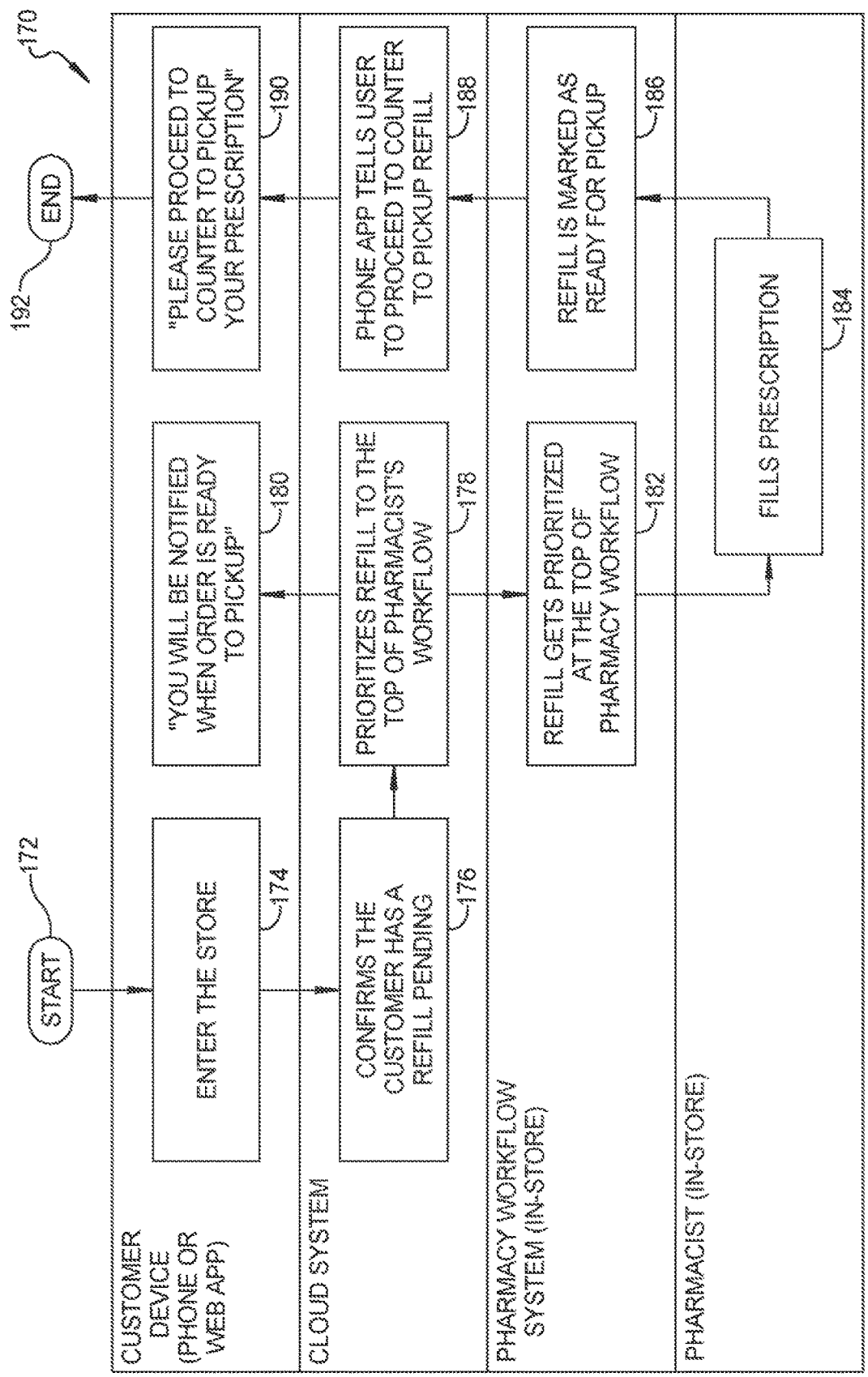
FIG. 10 is a flowchart of a method that may be used with the system shown in FIG. 1, according to an embodiment of the present invention.

Referring now to FIG. 10, an example method 170, according to one embodiment of the present invention, using the system 10 for mobile check-in with a pharmacy in the retail store by a mobile computing device 20 is illustrated. The method 170 can be executed by the components illustrated in FIGS. 1-9. In general, a flowchart of the method 170, according to one embodiment of the present invention, starts in bubble 172. The method 170 includes the steps of determining that a location of a customer entering or in the retail store in block 174. For example, receiving, by the system 10, a location of the customer entering or in the retail store can be determined by GPS of the mobile computing device 20 of the customer. The method 170 also includes the step of confirming that the customer has at least one prescription fill order pending with the pharmacy of the retail store in block 176. For example, performing a search, by the system 10, on a plurality of prescription fill order records corresponding to a plurality of prescription fill orders located in the pharmacy of the retail store 12, which may include inputting a search query to any search algorithm known in the art. The corpus of documents searched may include the database 48 of records or some other corpus of documents, accessible over the Internet. The method 170 includes the steps of prioritizing the at least one prescription fill order of the customer to a top of a workflow in the pharmacy of the retail store in block 178. For example, prioritizing, by the system 10, one or more of the prescription fill order records relevant to the customer in the search query. The method 170 also includes the steps of transmitting a communication to the mobile computing device 20 of the customer and displaying the communication on the mobile computing device 20 in block 180. For example, transmitting, by the system 10, a communication to the mobile computing device 20 of the customer that "You will be notified when order is ready for pickup". The method 170 includes the steps of prioritizing the at least one prescription refill order to the top of the workflow of the pharmacy in the retail store in block 182. For example, prioritizing, by the system 10, the at least one prescription fill order by moving the at least one prescription fill order of the customer to the top of the workflow of prescription orders to be filled by the pharmacist in the pharmacy of the retail store. The method 170 further includes the steps of filling the at least one prescription fill order by the pharmacist in block 184. For example, the pharmacist in the pharmacy of the retail store fills the at least one prescription fill order as directed by the at least one prescription fill order. The method 170 includes the steps of marking the at least one prescription fill order as ready for pickup in block 186. For example, marking, by the system 10, that the at least one prescription fill order is ready for pickup in the pharmacy of the retail store by the customer. For example, the pharmacist inputs on the user computing device 14 of the pharmacy that the at least one prescription fill order has been filled by the pharmacist. The method 170 also includes the step of transmitting a communication to the mobile computing device 20 of the customer for display by the mobile computer application to notify the customer to proceed to the counter in the pharmacy of the retail store to pick up the at least one filled prescription fill order in block 186. For example, transmitting, by the computer system 10, a communication to the mobile computing device 20 and the mobile computer application running on the mobile computing device 20 notifies the customer to proceed to the counter in the pharmacy of the retail store to pick up the at least one filled prescription fill order. The method 170 further includes the step of displaying with the mobile computer application running on the mobile device 20 the communication in block 190. For example, the mobile computer application displays the communication such as "Please proceed to counter to pick up your prescription" on the display of the mobile computing device 20 of the customer. The method 170 ends in block 192. It should be appreciated that the method includes other steps such as providing the computer system and servers and coupling the servers to one another.

In one embodiment, the pharmacy account server 40 may determine the triggering event to include an indication of a new prescription or a refilled prescription through the mobile webpage 1260. The pharmacy account server 40 may be programmed to receive a signal indicating a new or updated pharmaceutical drug associated with a pharmacy customer. The signal may include an indication of a new prescription and/or include a request to fill a prescription received from the mobile webpage 1260. In addition, the signal may include a pharmaceutical drug ID and a user ID. In one embodiment, the pharmacy account server 40 may access the pharmacy account list 46 being stored in the database an determine the user pharmacy account records 50 that is associated with the received user ID, determine one or more pharmaceutical drugs associated with the user ID, and determine the pharmaceutical drug ID associated with each corresponding pharmaceutical drug.

Figure 11A:
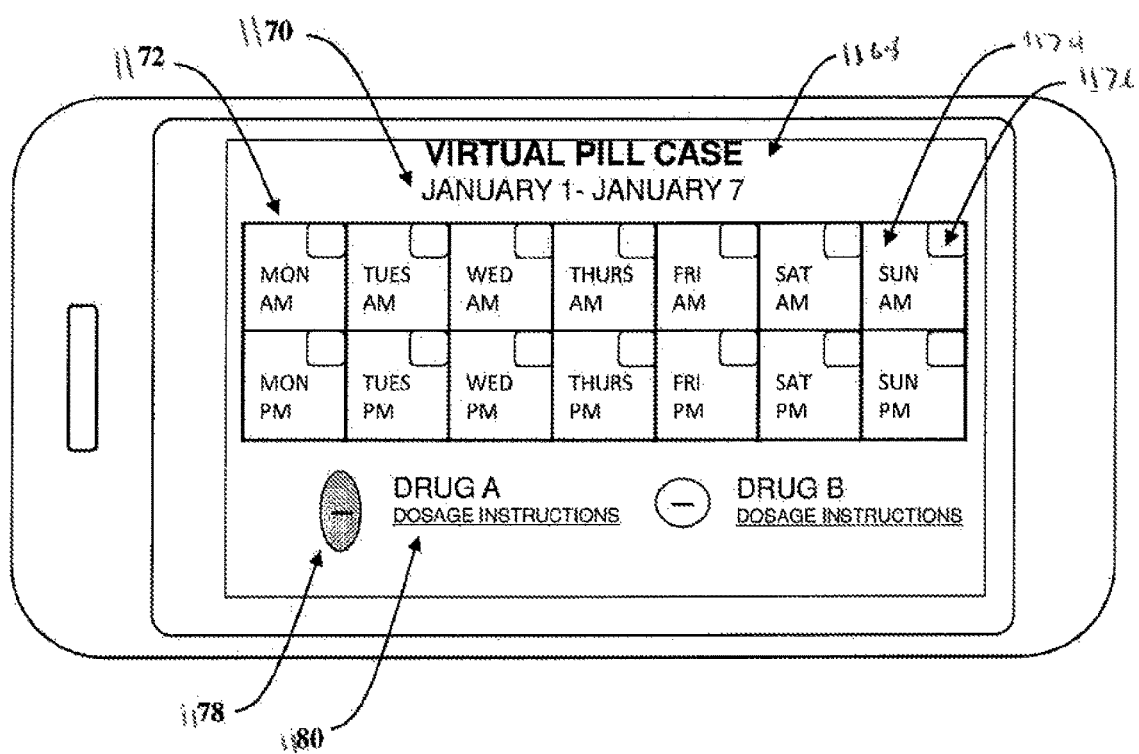
FIGS. 11-12 are illustrations of exemplary screenshots from the system of FIG. 1, according to an embodiment of the present invention.

Referring now to FIG. 11A, the pharmacy account server 40 may store the retrieved information about the prescribed pharmaceutical drug and the prescription information in a virtual pill case 1168 associated with the pharmacy customer. The virtual pill case 1168 may display a date range 1170. The date range 1170 may correspond to a calendar 1172, which may have a separate entry 1174 for each day of the week and, in some cases, entries for different times of day (e.g., AM and PM), similar to a traditional physical pill case. Each entry 1174 may have a checkbox 1176 to indicate whether the pharmacy customer has taken the prescribed dose for that day and/or time. An image 1178 showing the pill associated with the pharmaceutical drug may also be displayed, along with a hyperlink 1180 to additional information about the pharmaceutical drug including dosage instructions. All currently prescribed pharmaceutical drugs stored in database 46 and associated with the customer ID of the pharmacy customer will be shown in the virtual pill case 1168 (e.g., DRUG A and DRUG B).

Figure 11B:
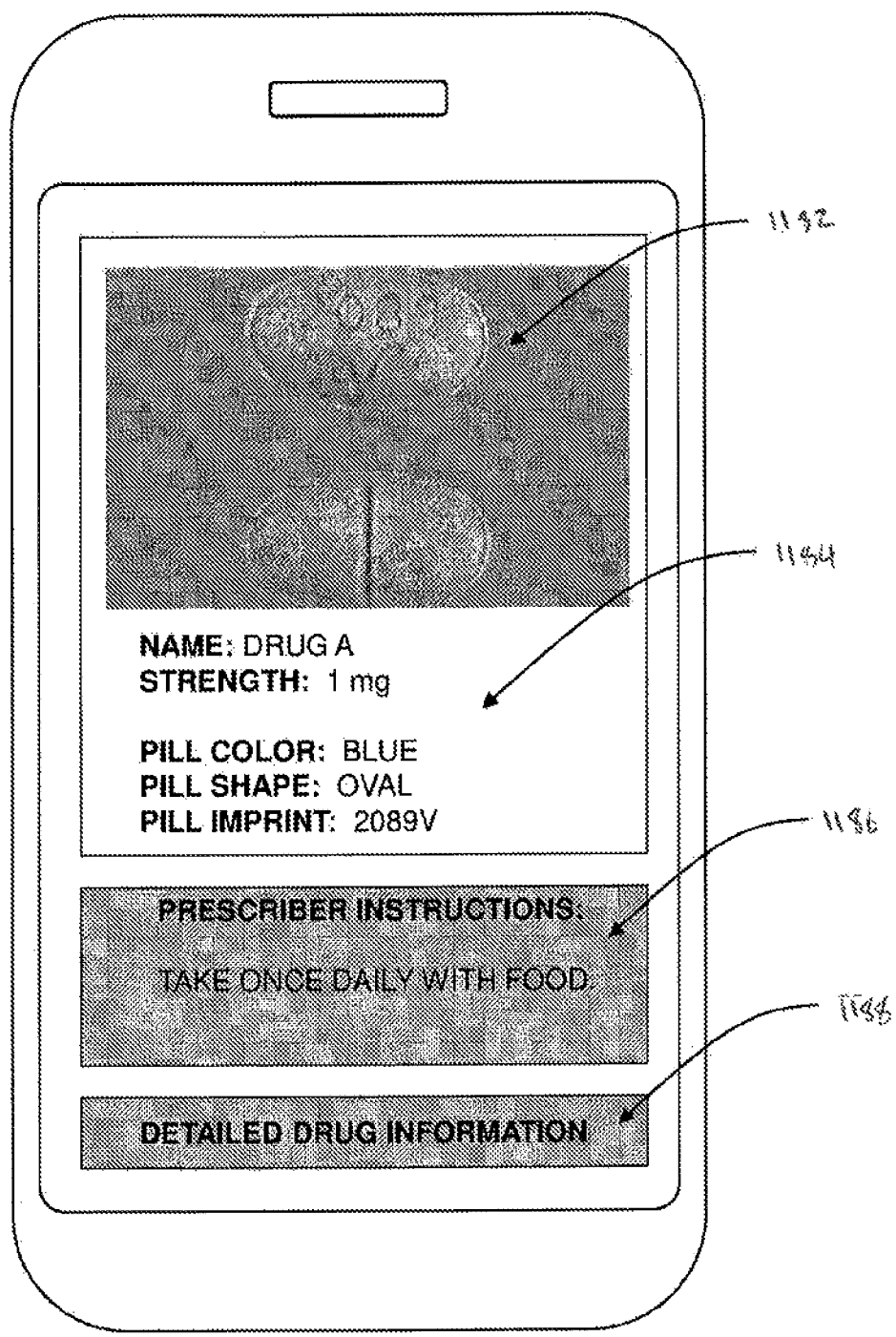

Referring now to FIG. 11B, when the pharmacy customer follows hyperlink 1180, the additional information about the pharmaceutical drug is displayed. In the illustrated embodiment, a photograph 1182 shows the pill (or other medication administration device) associated with the pharmaceutical drug. Drug details 1184 include, for example, the name, class, and strength of the drug, as well as the shape, color, and imprint of the pill. Additionally, dosage instructions 1186 are displayed, which include personalized instructions for administration of the medication as prescribed for the pharmacy customer. The pharmacy customer may access additional information via a hyperlink 1188, which may take the pharmacy customer to a third party website and display, for instance, information about side effects and drug and food interactions associated with the pharmaceutical drug.

Figure 11C:
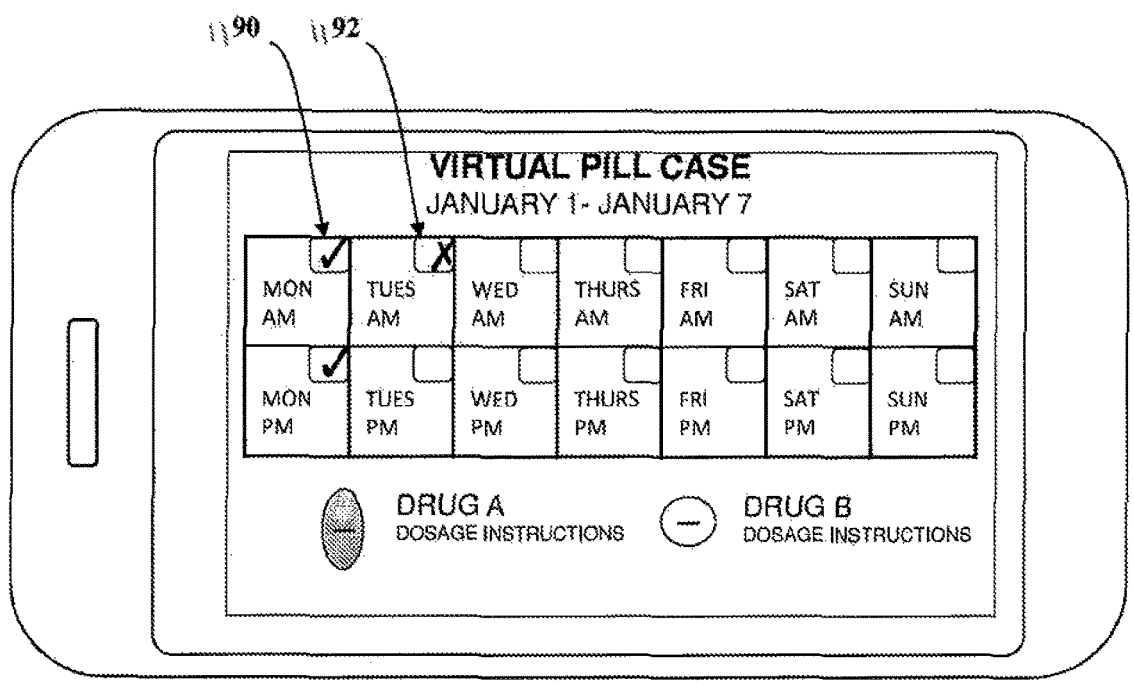

Referring now to FIG. 11C, the pharmacy customer may indicate that a dosage was taken by placing a taken dose symbol 1190. If the pharmacy customer misses a dose, a missed dose symbol 1192 may be shown. In response to a missed dose, a pharmacy notification may be sent to the pharmacy customer.

Figure 12:
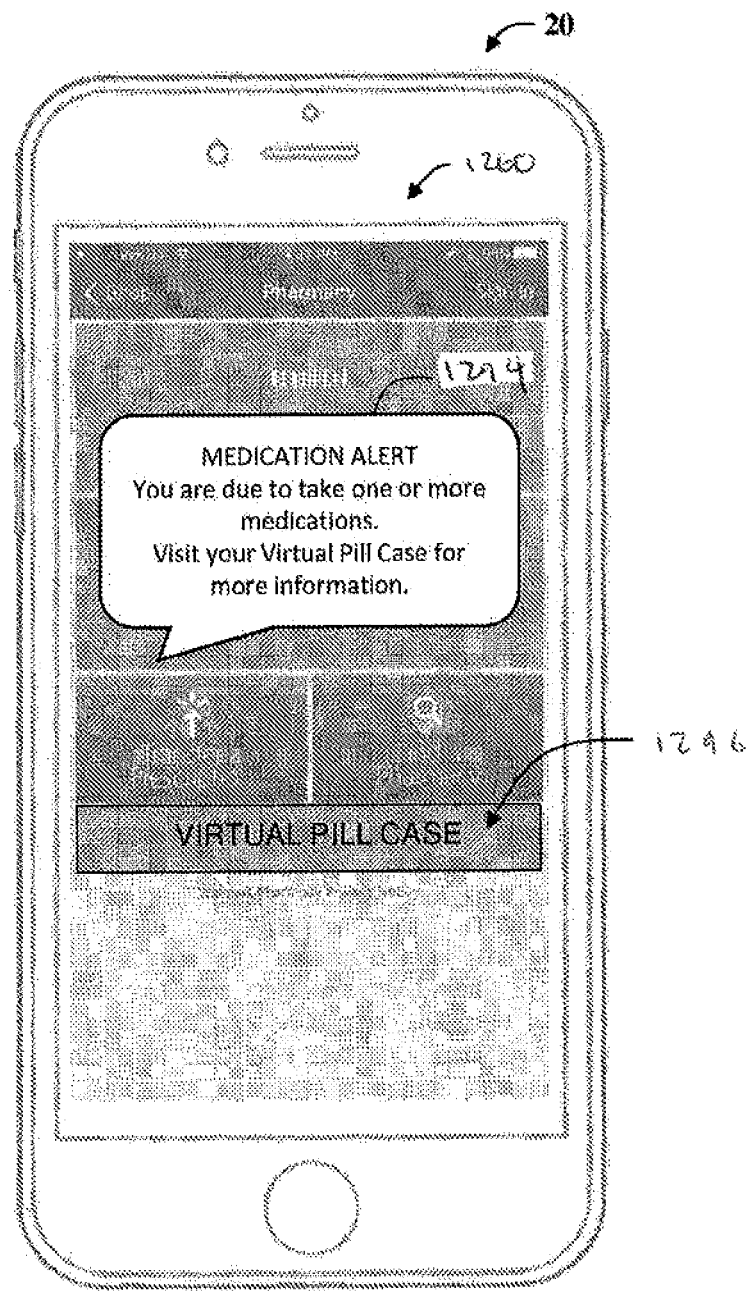

Referring now to FIG. 12, in one embodiment, the pharmacy account server 40 may receive a request to display a pharmacy notification message 1294 to the pharmacy customer via a user computing device 14. In one embodiment, the pharmacy account server 40 may receive a request to display the pharmacy notification message on a mobile computing device 20. The request may include a corresponding user ID. Upon receiving the request, the pharmacy account server 40 accesses the database 46 and identifies a user pharmacy account record 50 associated with the received user ID. The pharmacy account server 40 detects an occurrence of a triggering event as a function of the triggering event data, such as a missed dose by the pharmacy customer, and generates the pharmacy notification message 1294. The pharmacy account server 40 then generates and transmits a signal including the pharmacy notification message to the mobile computing device 20 to cause the mobile computing device 20 to display the pharmacy notification message on the mobile computing device 20.

FIGS. 13-16 are flowcharts of methods 1300, 1400, 1500, and 1600 that may be used with the system 10 for monitoring activities of pharmacy customers and generating and displaying information to the pharmacy customers on a website via a mobile computing device. The methods include a plurality of steps. Each method step may be performed independently of, or in combination with, other method steps. Portions of the methods may be performed by any one of, or any combination of, the components of the system 10.

Figure 13:
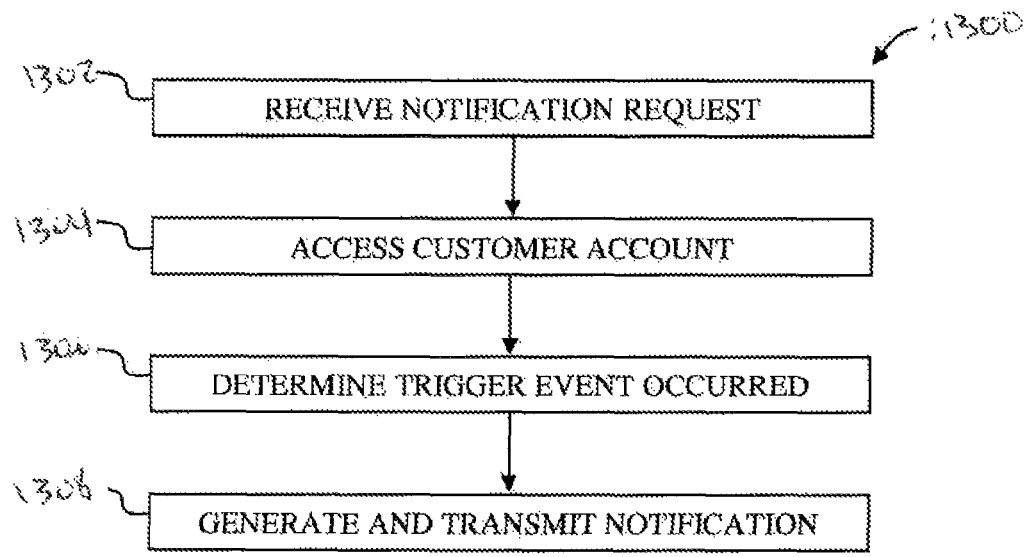
FIGS. 13-16 are flowcharts of methods that may be used with the system shown in FIG. 1, according to embodiments of the present invention.

Referring now to FIG. 13, a method 1300 for determining new prescription information is available is shown. At step 1302, the pharmacy account server 40 receives a request to initiate a notification operation to monitor an activity of a pharmacy customer. The request includes a corresponding user ID. In one embodiment, the request may be received from a mobile computing device 20 associated with a pharmacy customer. In another embodiment, the request may be initiated by the customer via the pharmacy website. In addition, the pharmacy account server 40 may be programmed to initiate a notification operation at a specific time and/or upon receiving an indication of activities associated with a pharmacy customer.

At step 1304, the pharmacy account server 40 accesses the user pharmacy account list 46 being stored in the database 46 to determine a user pharmacy account records 50 associated with the received user ID.

At step 1306, the pharmacy account server 40 determines that a triggering event has occurred. For example, in one embodiment, the triggering event may include a purchase of a new prescription by the pharmacy customer associated with the user ID. In another embodiment, the triggering event may include an indication that a pharmaceutical drug associated with the user ID requires a refill.

At step 1308, the pharmacy account server 40 generates and transmits a pharmacy notification message to the pharmacy customer requesting that the pharmacy customer add the new prescription information to the pharmacy customer's virtual pill case 1168. In the illustrated embodiment, the pharmacy account server 40 generates and transmits a signal including the notification message to the mobile computing device 20 to cause the mobile computing device 20 to display the notification message on the mobile computing device 20. For example, the pharmacy account server 40 may generate a notification upon detecting a new prescription or new refill. In one embodiment, the system 10 may access the corresponding user pharmacy account records 50 to determine a messaging API associated with an operating system of the mobile computing device 20 and generate the notification message as a function of the retrieved messaging API to enable the mobile computing device 20 to display the received message. In one embodiment, each user account record includes information associated with the mobile computing device 20 including a unique mobile ID and message API. In another embodiment, the user pharmacy account records 50 may include a message preferences, such as, for example, an email, text message, push messaging, automated phone call, and the like. The pharmacy account server 40 identifies the messaging preference associated with the user pharmacy account records 50 and generates the notification message based on the message preference.

Figure 14:
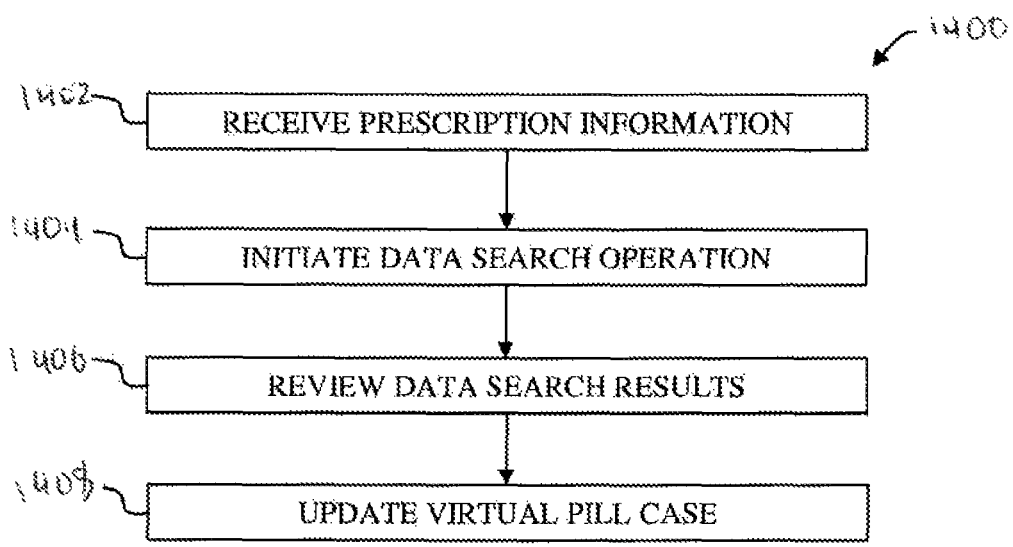

Referring now to FIG. 14, a method 1400 for acquiring new prescription information is shown. At step 1402, prescription information is received (e.g., manually entered by the pharmacy customer or received via an electronic transaction record).

At step 1404, the pharmacy account server 40 initiates a data search operation including transmitting the prescription information to the search engine server. In one embodiment, during the data search operation, the pharmacy account server 40 generates search terms associated with a prescribed pharmaceutical drug included in the identified user pharmacy account record 50 and transmits the search terms to the search engine server. The search engine server may initiate a search on the third party entity server 16. The search results may be transmitted from the search engine server to the pharmacy account server 40. The search results may include information about the pharmaceutical drug, including information about the pill shape, size, color, and strength, and an image or photograph representing the pill (or inhaler, pump, patch, or other device by which the pharmaceutical drug is administered).

At step 1406, the pharmacy account server 40 reviews the data search results and determines whether new information not already stored in the virtual pill case has been retrieved. For example, the prescription information may correspond to a refill of a pharmaceutical drug that is already stored in the pharmacy customer's virtual pill case, but the search results may indicate new information is available for the pharmaceutical drug because the manufacturer has changed the pill shape since the pharmacy customer's previous refill.

At step 1408, the virtual pill case is updated with any new information retrieved via the search results.

Figure 15:
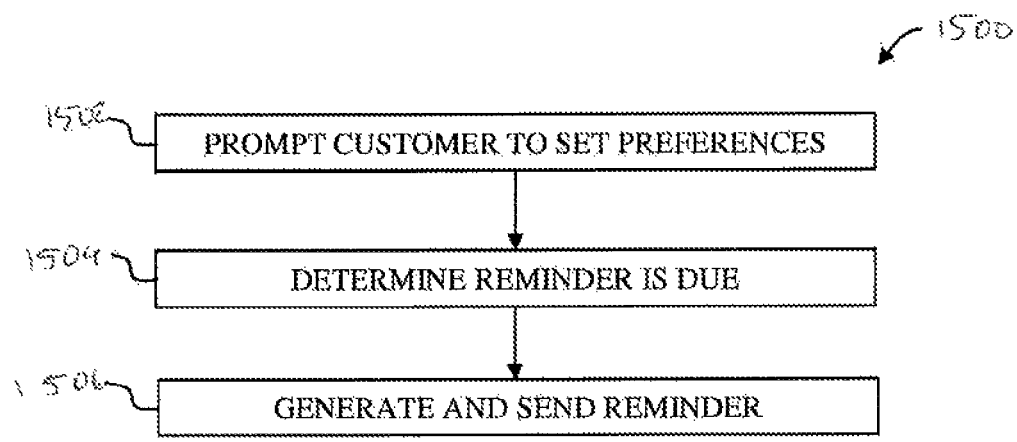

Referring now to FIG. 15, a method 1500 for sending a reminder to pharmacy customer regarding a virtual pill case. At step 1502, the pharmacy account server 40 prompts a pharmacy customer to set one or more reminder preferences regarding a virtual pill case. Reminder preferences may include, for example, whether the customer wishes to receive reminders regarding the virtual pill case. If the customer wishes to receive reminders, the customer may indicate a frequency with which the reminder should be sent (e.g., daily, weekly, etc.) and when the reminder should be sent (e.g., in the morning, afternoon, or evening, or at a specific time). The user may also indicate whether the reminder should be sent only if the user has missed a scheduled medication dose, or if the reminder should always be sent. Additionally, the user may indicate the preferred method of transmission of the reminder (e.g., push notification, text message, e-mail, etc.).

At step 1504, the pharmacy account server 40 determines that a reminder to the pharmacy customer is due, based on the customer's set reminder preferences. At step 1506, the pharmacy account server 40 generates and sends a reminder to the pharmacy customer regarding the virtual pill case.

Figure 16:
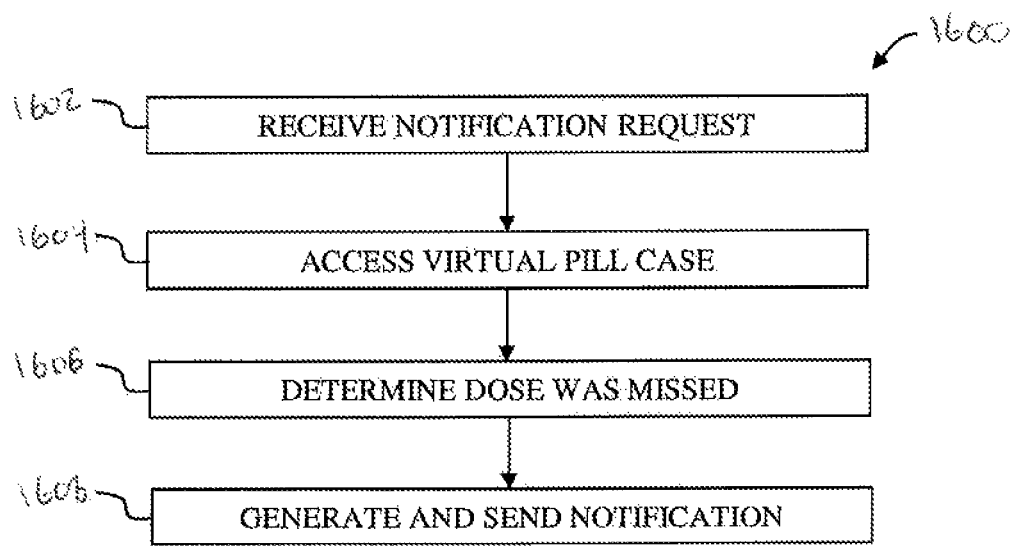

Referring now to FIG. 16, a method 1600 for sending a missed dose notification to pharmacy customer using a virtual pill case. At step 1602, the pharmacy account server 40 receives a request to initiate a notification operation to monitor an activity of a pharmacy customer. The request includes a corresponding user ID. In one embodiment, the request may be received from a mobile computing device 20 associated with a pharmacy customer. In another embodiment, the request may be initiated by the customer via the pharmacy website. In addition, the pharmacy account server 40 may be programmed to initiate a notification operation at a specific time and/or upon receiving an indication of activities associated with a pharmacy customer.

At step 1604, the pharmacy account server 40 accesses a virtual pill case associated with the pharmacy customer. At step 1606, the pharmacy account server 40 determines that the pharmacy customer missed at least one scheduled dose of a pharmaceutical drug according to dosage instructions provided by a prescriber. At step 1608, the pharmacy account server 40 generates and sends a notification to the pharmacy customer regarding the missed dose and prompting the user to visit the virtual pill case to review dosage instructions.

A controller, computing device, server or computer, such as described herein, includes at least one or more processors or processing units and a system memory (see above). The controller typically also includes at least some form of computer readable media. By way of example and not limitation, computer readable media may include computer storage media and communication media. Computer storage media may include volatile and nonvolatile, removable and non-removable media implemented in any method or technology that enables storage of information, such as computer readable instructions, data structures, program modules, or other data. Communication media typically embody computer readable instructions, data structures, program modules, or other data in a modulated data signal such as a carrier wave or other transport mechanism and include any information delivery media. Those skilled in the art should be familiar with the modulated data signal, which has one or more of its characteristics set or changed in such a manner as to encode information in the signal. Combinations of any of the above are also included within the scope of computer readable media.

The order of execution or performance of the operations in the embodiments of the invention illustrated and described herein is not essential, unless otherwise specified. That is, the operations described herein may be performed in any order, unless otherwise specified, and embodiments of the invention may include additional or fewer operations than those disclosed herein. For example, it is contemplated that executing or performing a particular operation before, contemporaneously with, or after another operation is within the scope of aspects of the invention.

In some embodiments, a processor, as described herein, includes any programmable system including systems and microcontrollers, reduced instruction set circuits (RISC), application specific integrated circuits (ASIC), programmable logic circuits (PLC), and any other circuit or processor capable of executing the functions described herein. The above examples are exemplary only, and thus are not intended to limit in any way the definition and/or meaning of the term processor.

In some embodiments, a database, as described herein, includes any collection of data including hierarchical databases, relational databases, flat file databases, object-relational databases, object oriented databases, and any other structured collection of records or data that is stored in a computer system. The above examples are exemplary only, and thus are not intended to limit in any way the definition and/or meaning of the term database. Examples of databases include, but are not limited to only including, Oracle® Database, MySQL, IBM® DB2, Microsoft® SQL Server, Sybase®, and PostgreSQL. However, any database may be used that enables the systems and methods described herein. (Oracle is a registered trademark of Oracle Corporation, Redwood Shores, Calif.; IBM is a registered trademark of International Business Machines Corporation, Armonk, N.Y.; Microsoft is a registered trademark of Microsoft Corporation, Redmond, Wash.; and Sybase is a registered trademark of Sybase, Dublin, Calif.).

The present invention has been described in an illustrative manner. It is to be understood that the terminology, which has been used, is intended to be in the nature of words of description rather than of limitation.

Many modifications and variations of the present invention are possible in light of the above teachings. Therefore, within the scope of the appended claims, the present invention may be practiced other than as specifically described.

What is claimed is:

1. A system comprising:
a computer system configured to receive input from and provide output to a mobile computing application for a retail store running on a mobile computing device of a customer, the computer system comprising:
one or more processors; and
one or more non-transitory computer-readable storage devices storing computing instructions configured to run on the one or more processors and perform acts of:
storing, in a pharmacy database, pharmacy account information, the pharmacy account information comprising:
a unique patient ID associated with the customer;
a pharmaceutical drug record indicating a pharmaceutical drug prescribed to the customer; and
an action record indicating triggering actions of the pharmaceutical drug;
determining a location of the customer entering or in the retail store;
confirming that the customer has at least one prescription fill order pending with a pharmacy of the retail store, wherein the at least one prescription fill order is for the pharmaceutical drug;
prioritizing the at least one prescription fill order to a top of a workflow of a pharmacist in the pharmacy of the retail store;
detecting a triggering action of the triggering actions comprising at least one of:
an environmental trigger; or
a purchase trigger;
in response to detecting the triggering action, facilitating a display, on the mobile computing device of the customer, of a notification about the triggering action;
transmitting a communication to the mobile computing device of the customer that the customer will be notified when the at least one prescription fill order is ready to be picked up at the pharmacy of the retail store;
receiving, from an electronic device of the pharmacist, an indication that the pharmacist has dispensed the pharmaceutical drug to the customer;
facilitating a display, on the mobile computing device of the customer, of a first user interface comprising a virtual pill case comprising:
a date range;
first prescription information about the pharmaceutical drug,
wherein:
the first prescription information comprises dosage instructions for the pharmaceutical drug; and
the pharmaceutical drug is scheduled to be taken by the customer during the date range;
a first image of the pharmaceutical drug;
a first customized hyperlink; and
a selectable user interface element corresponding to the pharmaceutical drug, the selectable user interface element configured to, when selected by the customer, indicate a use of the pharmaceutical drug by the customer; and
in response to receiving a selection of the first customized hyperlink, facilitating a display, on the mobile computing device of the customer, of a second user interface comprising:
a second image of the pharmaceutical drug, the second image of the pharmaceutical drug being larger than the first image of the pharmaceutical drug;
second prescription information about the pharmaceutical drug, the second prescription information comprising:
a name of the pharmaceutical drug;
a class of the pharmaceutical drug;
a dosage strength of the pharmaceutical drug;
a shape of the pharmaceutical drug;
a color of the pharmaceutical drug; and
an imprint of the pharmaceutical drug; and
a second customized hyperlink configured to navigate a web browser on the mobile computing device of the customer to a third-party website comprising side effect information about the pharmaceutical drug and adverse interaction information about the pharmaceutical drug.

2. A system as set forth in claim 1 wherein the computer system includes a server having a module to prioritize the at least one prescription fill order to the top of the workflow of the pharmacist.

3. A system as set forth in claim 1 wherein the computer system includes a server having a module to mark the at least one prescription fill order as ready for pick up by the customer from the pharmacy in the retail store.

4. A system as set forth in claim 1 wherein the computer system includes a server having a module to transmit a communication to the mobile computing device of the customer to proceed to a counter in the pharmacy of the retail store to pick up the at least one prescription fill order.

5. A system as set forth in claim 1 wherein the computer system includes a database that stores a plurality of prescription fill orders corresponding to the retail store.

6. A system as set forth in claim 1 wherein the computer system is configured to provide the communication to proceed to a counter to pick-up the at least one prescription fill order to the mobile computing device for display.

7. A system as set forth in claim 1 wherein the computer system is configured to receive a notification that the at least one prescription fill order has been filled by the pharmacist.

8. A system as set forth in claim 1 wherein the computer system is configured to perform a search on a plurality of prescription fill order records corresponding to a plurality of prescription fill orders in the retail store.

9. A system as set forth in claim 8 wherein a name of the customer is provided as part of a search query.

10. A system as set forth in claim 8 wherein a location of the retail store is provided as part of a search query.

11. A method comprising steps of:
storing, in a pharmacy database of a computer system, pharmacy account information, the pharmacy account information comprising:
a unique patient ID associated with a customer;
a pharmaceutical drug record indicating a pharmaceutical drug prescribed to the customer; and
an action record indicating triggering actions of the pharmaceutical drug;
determining, by the computer system, a location of the customer entering or in a retail store;
confirming, by the computer system, that the customer has at least one prescription fill order pending with a pharmacy of the retail store, wherein the at least one prescription fill order is for the pharmaceutical drug;

prioritizing, by the computer system, the at least one prescription fill order to a top of a workflow of a pharmacist in the pharmacy of the retail store;

detecting, by the computer system, a triggering action of the triggering actions comprising at least one of:
an environmental trigger; or
a purchase trigger;

in response to detecting the triggering action, facilitating a display, on a mobile computing device of the customer, of a notification about the triggering action;

transmitting a communication to the mobile computing device of the customer that the customer will be notified when the at least one prescription fill order is ready to be picked up at the pharmacy of the retail store;

receiving, from an electronic device of the pharmacist, an indication that the pharmacist has dispensed the pharmaceutical drug to the customer;

facilitating a display, on the mobile computing device of the customer, of a first user interface comprising a virtual pill case comprising:
a date range;
first prescription information about the pharmaceutical drug, wherein:
the first prescription information comprises dosage instructions for the pharmaceutical drug; and
the pharmaceutical drug is scheduled to be taken by the customer during the date range;
a first image of the pharmaceutical drug;
a first customized hyperlink; and
a selectable user interface element corresponding to the pharmaceutical drug, the selectable user interface element configured to, when selected by the customer, indicate a use of the pharmaceutical drug by the customer; and in response to receiving a selection of the first customized hyperlink, facilitating a display, on the mobile computing device of the customer, of a second user interface comprising:
a second image of the pharmaceutical drug, the second image of the pharmaceutical drug being larger than the first image of the pharmaceutical drug;
second prescription information about the pharmaceutical drug, the second prescription information comprising:
a name of the pharmaceutical drug;
a class of the pharmaceutical drug;
a dosage strength of the pharmaceutical drug;
a shape of the pharmaceutical drug;
a color of the pharmaceutical drug; and
an imprint of the pharmaceutical drug; and
a second customized hyperlink configured to navigate a web browser on the mobile computing device of the customer to a third-party website comprising side effect information about the pharmaceutical drug and adverse interaction information about the pharmaceutical drug.

12. A method as set forth in claim 11 including the steps of prioritizing, by a server having a module, the at least one prescription fill order to the top of the workflow of the pharmacist.

13. A method as set forth in claim 11 including the steps of marking, by a server having a module, the at least one prescription fill order as ready for pick up by the customer from the pharmacy in the retail store.

14. A method as set forth in claim 11 including the steps of transmitting, by a server having a module, a communication to the mobile computing device of the customer to proceed to a counter in the pharmacy of the retail store to pick up the at least one prescription fill order.

15. A method as set forth in claim 11 including the steps of storing in a database a plurality of prescription fill orders corresponding to the retail store.

16. A method as set forth in claim 11 including the steps of transmitting, by a server having a module, a communication to proceed to a counter to pick-up the at least one prescription fill order to the mobile computing device for display.

17. A method as set forth in claim 11 including the steps of notifying the computer system that the at least one prescription fill order has been filled by the pharmacist.

18. A method as set forth in claim 11 including the steps of performing, by the computer system, a search on a plurality of prescription fill order records corresponding to a plurality of prescription fill orders in the retail store.

19. A method as set forth in claim 18 wherein a name of the customer is provided as part of a search query.

20. A method as set forth in claim 18 wherein a location of the retail store is provided as part of a search query.

21. One or more non-transitory computer-readable storage media, having computer-executable instructions embodied thereon, wherein when executed by at least one processor, the computer-executable instructions cause the processor to:
store, in a pharmacy database, pharmacy account information, the pharmacy account information comprising:
a unique patient ID associated with a customer;
a pharmaceutical drug record indicating a pharmaceutical drug prescribed to the customer; and
an action record indicating triggering actions of the pharmaceutical drug;
determine a location of the customer entering or in a retail store;
confirm that the customer has at least one prescription fill order pending with a pharmacy of the retail store, wherein the at least one prescription fill order is for the pharmaceutical drug;
prioritize the at least one prescription fill order to a top of a workflow of a pharmacist in the pharmacy of the retail store;
detect a triggering action of the triggering actions comprising at least one of:
an environmental trigger; or
a purchase trigger;
in response to detecting the triggering action, facilitate a display, on a mobile computing device of the customer, a notification about the triggering action;
transmit a communication to the mobile computing device of the customer that the customer will be notified when the at least one prescription fill order is ready to be picked up at the pharmacy of the retail store;
receive, from an electronic device of the pharmacist, an indication that the pharmacist has dispensed the pharmaceutical drug to the customer;
facilitate a display, on the mobile computing device of the customer, of a first user interface comprising a virtual pill case comprising:
a date range;
first prescription information about the pharmaceutical drug, wherein:
the first prescription information comprises dosage instructions for the pharmaceutical drug; and the pharmaceutical drug is scheduled to be taken by the customer during the date range;
a first image of the pharmaceutical drug;
a first customized hyperlink; and
a selectable user interface element corresponding to the pharmaceutical drug, the selectable user interface element configured to, when selected by the customer, indicate a use of the pharmaceutical drug by the customer; and
in response to receiving a selection of the first customized hyperlink, facilitate a display, on the mobile computing device of the customer, of a second user interface comprising:
a second image of the pharmaceutical drug, the second image of the pharmaceutical drug being larger than the first image of the pharmaceutical drug;
second prescription information about the pharmaceutical drug, the second prescription information comprising:
a name of the pharmaceutical drug;
a class of the pharmaceutical drug;
a dosage strength of the pharmaceutical drug;
a shape of the pharmaceutical drug;
a color of the pharmaceutical drug; and
an imprint of the pharmaceutical drug; and
a second customized hyperlink configured to navigate a web browser on the mobile computing device of the customer to a third-party website comprising side effect information about the pharmaceutical drug and adverse interaction information about the pharmaceutical drug.

* * * * *